US011547387B2

(12) United States Patent
Forzoni et al.

(10) Patent No.: US 11,547,387 B2
(45) Date of Patent: Jan. 10, 2023

(54) ULTRASOUND PROBE AND ULTRASOUND SYSTEM PROVIDED WITH SAID ULTRASOUND PROBE

(71) Applicant: ESAOTE SpA, Genoa (IT)

(72) Inventors: Leonardo Forzoni, Florence (IT); Stefano De Beni, Genoa (IT); Fabrizio Spezia, Giussano (IT)

(73) Assignee: Esaote S.p.A., Genoa (IT)

( * ) Notice: Subject to any disclaimer, the term of this patent is extended or adjusted under 35 U.S.C. 154(b) by 777 days.

(21) Appl. No.: 16/256,881

(22) Filed: Jan. 24, 2019

(65) Prior Publication Data
US 2019/0239852 A1  Aug. 8, 2019

(30) Foreign Application Priority Data

Feb. 7, 2018 (EP) ..................................... 18155460

(51) Int. Cl.
*A61B 8/00* (2006.01)

(52) U.S. Cl.
CPC .......... *A61B 8/4254* (2013.01); *A61B 8/4455* (2013.01); *A61B 8/4209* (2013.01); *A61B 8/4422* (2013.01); *A61B 8/4433* (2013.01)

(58) Field of Classification Search
CPC .................................................... A61B 8/4254
See application file for complete search history.

(56) References Cited

U.S. PATENT DOCUMENTS

| | | |
|---|---|---|
| 5,758,650 A | 6/1998 | Miller |
| 9,271,682 B2 | 3/2016 | Cerofolini et al. |
| 2006/0191344 A1* | 8/2006 | Hashimoto .............. A61B 8/00 73/632 |
| 2009/0266957 A1 | 10/2009 | Cermak |
| 2013/0085391 A1* | 4/2013 | Matsumura .......... A61B 8/4411 600/443 |
| 2014/0073929 A1* | 3/2014 | Mehi .................... A61B 8/0841 600/472 |
| 2015/0223774 A1 | 8/2015 | Ikeda |
| 2016/0262722 A1 | 9/2016 | Marmor |
| 2017/0284971 A1* | 10/2017 | Hall ....................... G01B 5/012 |
| 2018/0140274 A1* | 5/2018 | Sandrin ................ A61B 8/4455 |

FOREIGN PATENT DOCUMENTS

| | | |
|---|---|---|
| EP | 1 167 996 A1 | 1/2002 |
| EP | 1 467 317 A1 | 10/2004 |
| EP | 1 681 019 A1 | 7/2006 |
| EP | 1 932 477 A1 | 6/2008 |
| EP | 2 147 636 A1 | 1/2010 |
| EP | 2 368 514 A1 | 9/2011 |
| GB | 2 507 987 A | 5/2014 |
| JP | 2007 205519 A | 8/2007 |

OTHER PUBLICATIONS

European Search Report dated Jul. 19, 2018, which issued in the corresponding European Patent Application No. 18155460.1.

* cited by examiner

*Primary Examiner* — Bill Thomson
*Assistant Examiner* — Aminah Asghar
(74) *Attorney, Agent, or Firm* — Dickinson Wright PLLC

(57) ABSTRACT

An ultrasound probe in combination with at least an operating unit such as a tracking sensor or receiver and/or a keypad and/or a surgical tool support, wherein the probe and the at least one operating unit are each one provided with one of two parts of a releasable joint, the said two parts of the joint being releasably engageable one with the other by magnetic force and by mechanical coupling.

10 Claims, 14 Drawing Sheets

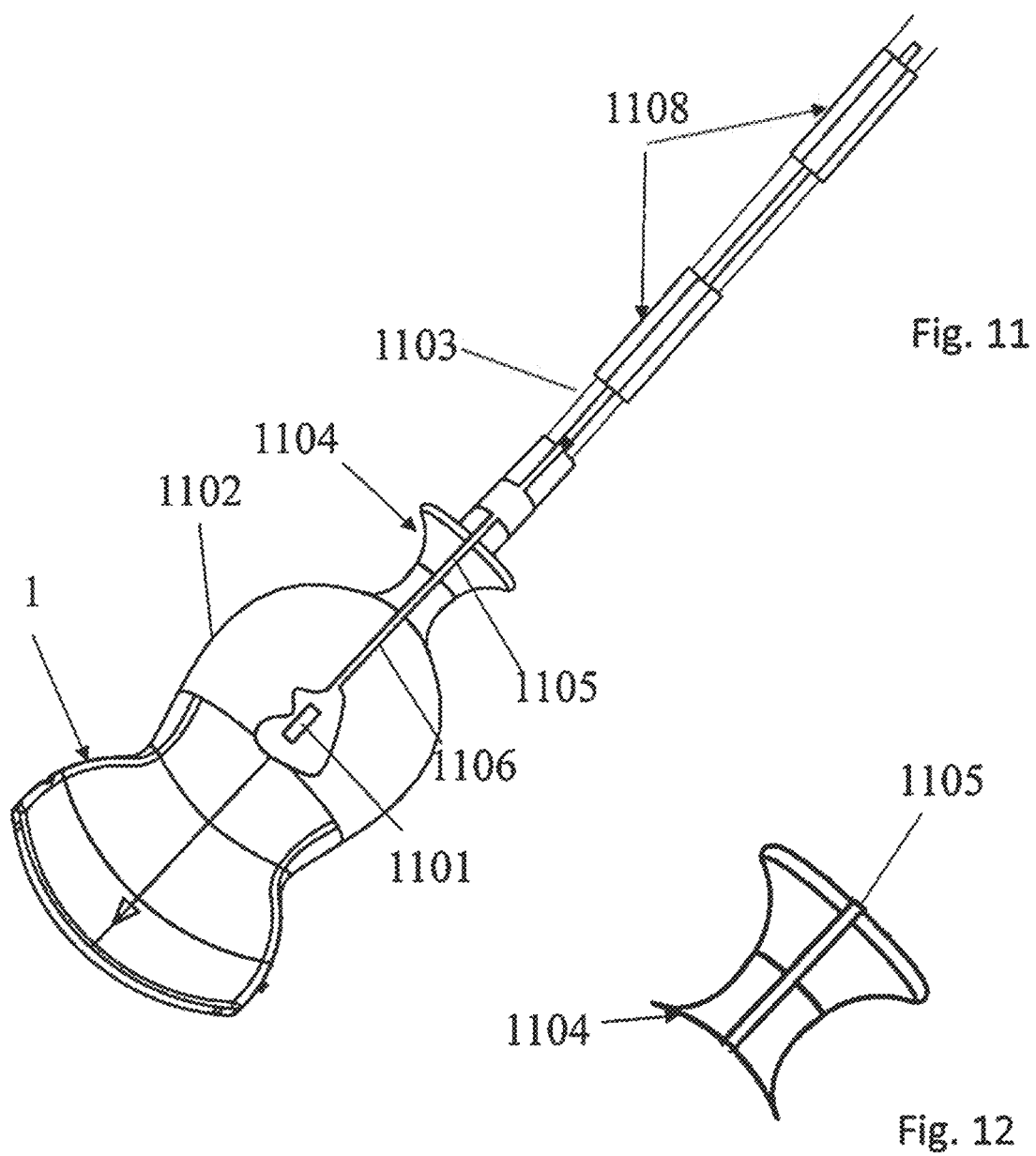
Fig. 11
Fig. 12
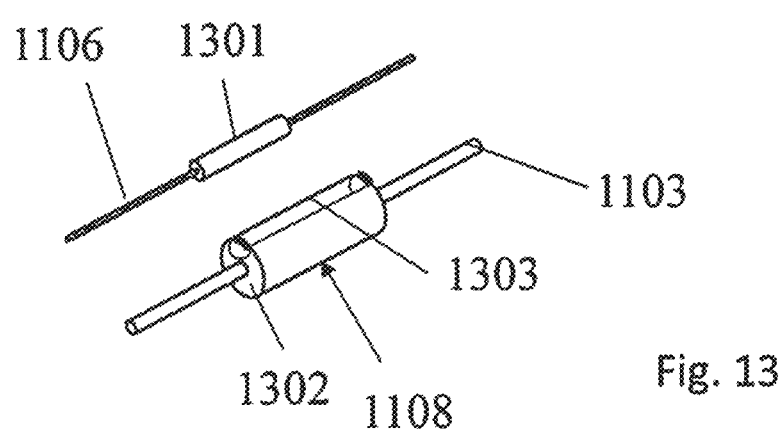
Fig. 13

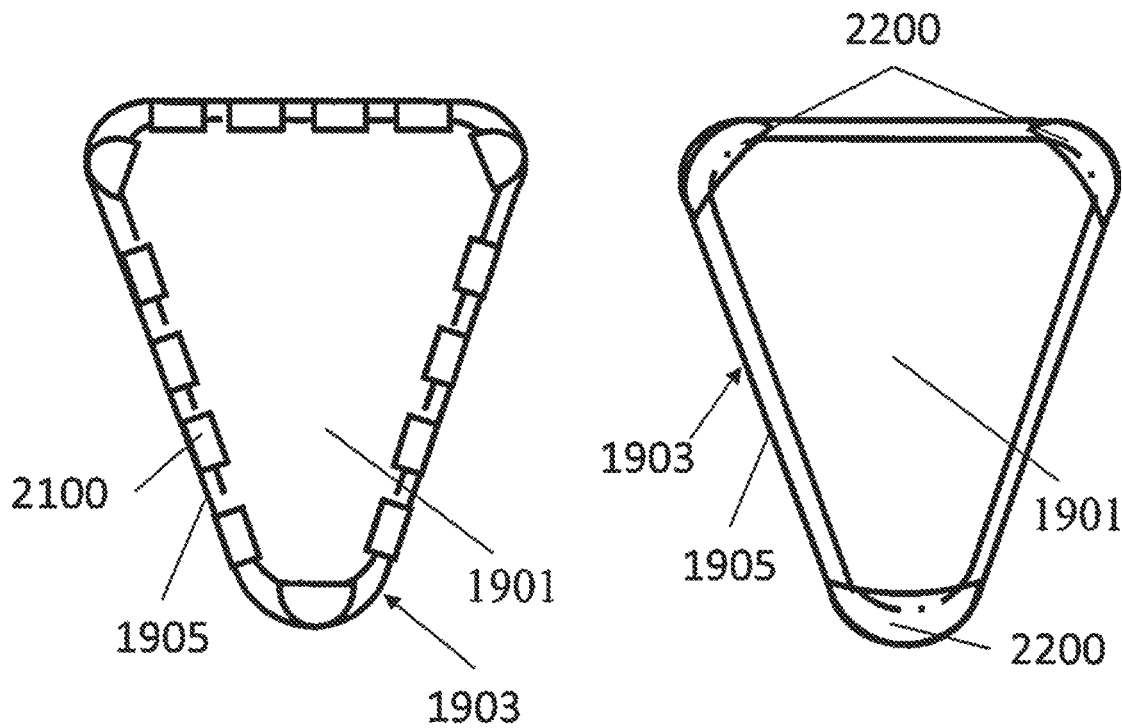
Fig. 21
Fig. 22
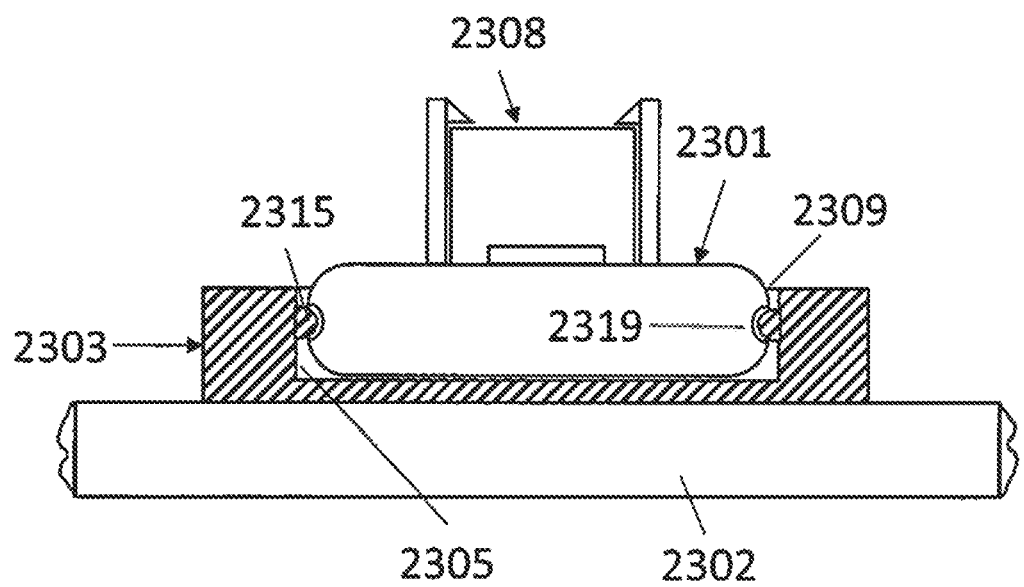
Fig. 23

ULTRASOUND PROBE AND ULTRASOUND SYSTEM PROVIDED WITH SAID ULTRASOUND PROBE

BACKGROUND OF THE INVENTION

Ultrasound imaging may be used for acquiring three-dimensional images, for guiding surgical tools such as biopsy needles, for navigating in real time anatomical districts in which surgical interventions has to be carried out or prosthesis has to be placed. Imaging techniques are also wide spread in which the image is generated as a combination of images of a target body or region which images acquired with different imaging techniques one these techniques being ultrasound imaging. These combined images require registration of the images acquired by the different imaging techniques before fusing, or compounding together in another way the single images.

In all the above cases, there is the need of tracking the position of the ultrasound probe and to refer this position to a common reference system.

According to an example, in acquiring three-dimensional ultrasound images, many two-dimensional images may be acquired, each one along a different slice of a plurality of adjacent slices and the relative position of each image slice is determined by tracking the displacement of the probe along the body of the target. This requires that the probe is provided in combination with a tracking system allowing to determine the probe position and/or orientation.

A further example consists in the so called virtual navigator real time fusion technology. This technology is used to enhance real-time ultrasound scans with second imaging modality 3D acquisitions, thereby supplementing MRI, CT, PET, PET/MRI, PET/CT, AngioCT, MRI TOF, 3D Ultrasound, 3D CEUS (Contrast Enhanced Ultrasound), 3D Color or Power Doppler data with morphological (B-Mode), hemodynamic (Color, Power, Continuous or Pulsed Wave Doppler), CEUS and stiffness (Elastosonography) data. Fusing together these real-time diagnostics supplied by ultrasound with the highly detailed anatomical volumes (offered by MRI or CT), or functional (offered by PET, PET/MRI, PET/CT, AngioCT, MRI TOF, 3D Color or Power Doppler, 3D CEUS), allows the operator to display in real-time a virtual space where the different imaging modes are merged and where ultrasound scanning plane spatial data is correlated with three-dimensional second imaging modality volumes. This allows for an easier navigation that is based on the geometrical and spatial relationships between the real-time data and pre-acquired data. The tool can be used for prevention, diagnosis, therapy, intervention and follow up. Virtual Navigator techniques are based on a tracking technology used in conjunction with ultrasound probes with or without biopsy instruments or other surgical tools. In some applications, also an accurate motion compensation is provided for compensating the voluntary and/or involuntary movements of the patient during imaging. According to an embodiment a motion control sensor is placed on the body being examined to counteract voluntary and/or involuntary movements and to enable continuous motion compensation which preserves the previously set co-registration between two, or more than two, imaging modes. Some examples of these techniques are disclosed for instance in document U.S. Pat. No. 9,271,682 assigned to the present applicant. In this document a method and a system are disclosed for operating an imaging device for the monitoring of an anatomical region during insertion of metallic objects or objects made at least partly of metal inside the said region, which metallic objects disturb standard tracking ultrasound probe systems. The method is based on acquisition of image data by two different imaging systems, one of which is capable of high resolution and the other of real time imaging, registering the images of the two imaging systems and using the high resolution system for imaging the anatomic district while the real time imaging system is used for imaging the metallic object to be introduced in the said anatomic district. Document EP1467317 discloses a method and an apparatus for combining first and second imaging data of an object, according to which an ultrasound detector repeatedly generates the first image data of the object and the second image data of the object are generated separately by means of a CT an MR a PET or an X-Ray apparatus. The second image data being three-dimensional image data of the object. A combination device combines the first and second image data. A tracker of the ultrasound probe being provided for tracking the position of the ultrasound probe and of the two-dimensional data generated by the ultrasound probe. The tracking device is used as a reference coordinate system in relation to which first and second image data can be registered in order to register first and second image data for combination. A certain position of the ultrasound probe and thus of the slice or section plane along which the image data is collected can be thus related to an identical section plane or slice in the three-dimensional image data allowing reconstruction of the image along the said slice or section plane by using the second image data instead of the first image data generated by the ultrasound probe. Document EP2147636 discloses a device for guiding surgical tools by ultrasonic imaging. From 3D images, 2D images are generated corresponding to a view from the tip of the tool. A tracking system is provided in combination with the ultrasound imaging system which tracking system determines the position and orientation of the probe and of the surgical tool. The tracking system comprising a tracking unit cooperating with sensors such as transponders associated to the probe and to the surgical tool.

In all the above disclosed cases, an operating unit must be secured to the ultrasound probe. When the probe motion, position and/or orientation in space has to be determined by a tracking system, the operating unit can be a sensor secured to the probe which measures parameters of a coded field permeating the space within which the probe has to be displaced or one or more markers positioned on the probe and which are sensed by a sensing unit furnishing information about position, orientation ad motion (displacement) of the probe. One known example of tracking system is a so called electromagnetic tracking system. Another example is represented by an optical tracking system.

In the electromagnetic tracking systems, a coded electromagnetic filed is generated permeating the region in which the probe has to be positioned and displaced and the probe is provided with at least one electromagnetic sensor or receiver measuring the electromagnetic filed. This measured data are transmitted to a processing unit of the tracking system determining the position of the probe in relation to a fixed reference position for example the origin of the electromagnetic field.

Optical tracking systems uses a combination of optical markers having a precise relative position on a support. The support is secured to the probe and the markers are sensed by an optical detector. The data of the relative position of the markers revealed by the optical sensor allows to determine position, orientation and displacement of the probe.

The electromagnetic system of tracking the probe, for example in real-time fusion imaging, combining ultrasound images and one or more second imaging modality/ies (MRI, CT, PET, PET/MRI, PET/CT, AngioCT, MRI TOF, 3D Ultrasound, 3D CEUS, 3D Color or Power Doppler) represents a good choice in terms of ergonomics and usability, with respect to the optical trackers. The electromagnetic tracker has the main limitation of the necessity of being close (max 78 cm) to the transmitter which generates the electromagnetic field in the region where the probe is positioned and displaced. Furthermore, electromagnetic tracking systems are influenced by metallic parts for example of the examination bed and/or by the power cords and also by external electromagnetic fields. On the other hand the electromagnetic tracking systems have the plus of having a small dimensions (usually 0.7×0.7×2.0 cm), of being easily mountable on the probe without changing in a significant and/or limiting way the probe shape and/or the weight of the probe, so that the probe maintains essentially its ergonomic features and do not alter its behavior in relation to the manipulation by the user. This effect is, instead, obtained with the optical tracking systems. Optical tracking systems have the advantage to enables to be operated quite distant from the optical detector (which has anyway to maintain the line of sight—condition not always met within the crowded clinical/interventional environments). Moreover, the optical tracker changes consistently probe dimensions and weight relationships and influence the ergonomics and the behavior of manipulation by the user. The use of a sterile cover (quite common in any interventional setting) is impossible in case of optical tracker (covering the whole probe plus tracking sensor), such as, for example, of the electromagnetic type, while it is common and easy to be used, in case of a single sensor, and easily positioned and removed (covering both probe and sensor, avoiding any disinfection/sterilization of the tracking sensor.

In any case in both tracking systems at least a sensor or at least an optical marker needs to be secured to the probe. Current solutions provide for two embodiments. According to a first embodiment the operating unit is secured to the ultrasound probe by a mechanical joint or attachment device. This embodiment may be provided in two variants in one variant the joint or the attachment device is not releasable, in the sense that one secured to the probe the sensor may not be separated anymore from the probe. The second variant provides for releasable joint or attachment devices of the operating unit to the probe, allowing the operating unit to be separated from the probe when not in use.

According to a second known embodiment the operating units, i.e. the sensors or the markers of the tracking system which has to be mounted on the probe may be integrated steadily in the probe structure.

When the probe is used as a support for a surgical tool such as a biopsy needle, the sensor or markers can be integrated or secured to the support for the surgical tool which can be secured to the probe for example by mechanical connection.

Still further embodiments require that the probe is provided with at least one button or several buttons on small keypads which are also to be secured to the probe body. Also in this case the above variants and embodiments are used and known. A button or a keypad can be steadily integrated in the structure of the probe or the button or the keypad can be secured by releasable joints or by fixed joints to the probe in a similar way as for the sensors and markers.

The most frequent position on a probe of an electromagnetic sensor or receiver of a tracking system is on the probe body and particularly on the probe handle or within the probe itself. While the construction of a probe with the tracking sensor inside is something already available on the market, this solution is far from being an industrial-optimization choice, since the costs for such a dedicated probe are too high in relation to the relatively low volumes of production.

The solution most commonly used today is the one of having the electromagnetic sensor attached externally on the probe body, by a mechanically attached sensor support. This solution is efficient in terms of sensor attachment stability, reduced weight and reduced impact on probe ergonomics and handling. On the other hand it's not easy to be attached/removed especially "on the fly" for instance if the probe and the sensor are already covered with the sterile sheet.

BRIEF SUMMARY OF THE PRESENT INVENTION

According to a first object a combination of a probe and an operating unit such as a tracking sensor or receiver and/or a keypad and/or a surgical tool support is aimed in which a releasable joint of the operating unit to the probe is provided, the said joint having relatively small dimensions not impacting on the shape of the probe and on ergonomic features of the probe and allowing easy attachment and detachment of the operating unit from the probe especially on the fly.

According to a further aspect the joint should have reduced weight and should not alter the balance of the probe shape in the hand of the user, not altering the behavior of the probe during manipulation.

Still a further aspect aims to providing a joint between the probe and the operating unit which allows to be configured according to different modalities of engagement between the probe and the operating unit and/or according to different strength of the retaining force or bonding force of the operating unit to the probe.

Another aspect relates to providing a combination of a probe and an operating unit, such as a tracking sensor or a receiver and/or a keypad and/or a surgical tool support comprising a releasable joint of the operating unit to the probe, the manipulation and operation of the joint in securing the operating unit to the probe and in detaching the operating unit from the probe being intuitive and requiring to exercise low manual forces for attaching and detaching the operating unit to and from the probe.

According to still another aspect an ultrasound system is aimed being provided in combination with a probe and with at least an operating unit which can be releasably attached to the probe, the operating unit being part of an operating system executing imaging related functions.

According to an aspect the operating unit is at least a sensor, a receiver or a marker of a probe tracking system provided in combination with the ultrasound system.

According to still an aspect of the invention the operating unit is a surgical tool support for releasably securing the surgical tool to the probe and the ultrasound system being provided in combination with a system for tracking the surgical tool and/or the probe.

In relation to the first aspect an ultrasound probe is provided in combination with an operating unit such as a tracking sensor or receiver and/or a keypad and/or a surgical/interventional tool support, the probe and the operating unit being each one provided with one of two parts of a releasable joint, the said two parts of the joint being releasably engageable one with the other by magnetic force and by mechanical coupling.

According to an embodiment the part of the joint provided on the probe is secured to the probe body. A variant provides for integrating the said part of the joint in the probe structure.

An alternative variant provides for securing the said part of the joint in a releasable way to the probe.

According to a preferred embodiment the part of the joint on the probe is provided on the handle of the probe or integrated in the structure of the handle of the probe.

Similarly, according to an embodiment, the part of the joint associated to the operating unit is integrated or non-releasably secured to the operating unit, particularly to its case or a part of its case.

In a variant embodiment, the part of the joint associated to the operating unit is releasably secured to the structure of the operating unit, particularly to the case of the said operating unit.

In an embodiment, the operating unit is secured to the associated part of the joint, i.e. the part of the joint dedicated to be secured to the said operating unit, by means of a mechanical coupling. In a variant embodiment, the said mechanical coupling is a snap coupling.

The above variant embodiments relating to the way the probe and the operating unit are secured to the relating parts of the joint may be provided in any combination one with the other.

In relation to the part or the joint associated to the operating unit, in a variant embodiment the said part of the joint can form the support to which two or more operating units can be secured to the said joint according to one or more of the above described variant embodiments, the said two or more operating units being identical or different operating units.

According to an embodiment the total force securing the operating unit or the two or more operating units to the probe, i.e. the force retaining engaged one to the other the two parts of the joint is produced in part by magnetic force and in part by the mechanical coupling.

According to a further embodiment which can be provided in any combination with the preceding ones a guide for the correct positioning of the two parts of the joint is provided, the said guide being formed by the magnetic attraction force between the two parts of joint.

According to another feature which can be provided in any combination with the above embodiments centering means between the two parts of the joint are provided which centering means are or are part of the mechanical coupling between the two parts of the joint.

Thanks to the above configuration of the joint, a magnetic guidance of the two parts of the joint is provided which is combined with a mechanical low profile attachment.

Particularly when the operating unit is a sensor or a receiver of an electromagnetic field of an electromagnetic tracking system provided in combination with the probe, the magnetic field sources on the probe and on the part of the joint associated to the operating unit are shielded towards the probe and towards the operating unit by magnetic shields.

According to an embodiment the magnetic shields comprise each one a non-magnetic plate.

In an embodiment, in combination with the magnetic shields on the prove and on the part of the joint associated to the operating unit on the respectively facing sides of the part of the joint on the probe and of the part of the joint associated to the operating unit there are at least one or more magnetic seeds distributed according to a predefined pattern and having opposed polarity so that the part of the joint of the probe and the part of the joint associated to the operating unit are attracted one against the other.

In an embodiment herein the probe has a case, the case comprising a case wall, the part of the joint on the probe comprising a layer of magnetic insulating material having a predetermined dimension and shape which layer is laid over the surface of the case wall facing the interior of the probe, one or more magnetic elements or magnetic seeds being distributed according to a predefined pattern between the layer of magnetic insulating material and the wall of the case of the probe.

Relating to an embodiment of the part of the joint associated to one or more operating units and which is adapted to cooperate with the above embodiment of the part of the joint on the probe, the said part of the joint associated to the one or more operating units comprises a socket provided with a contact surface facing the external surface of the wall of the case of the probe coincident with the internal layer of magnetic insulating material and the magnetic elements, the said contact surface being covered with a magnetic insulating material and the said layer of magnetic insulating material bearing on the side facing the probe one or more magnetic elements which are positioned and polarized in a way as to interact in an attracting manner with the pattern of one or more magnetic elements on the probe.

In the following, more detailed and specific embodiments will be disclosed.

In an embodiment, the case of the probe is made of plastic material at least in the region in which the layer of magnetic insulating material is provided, while at least the magnetic elements and/or the layer of insulating material are bond or integrated in the material of the case of the probe during the molding process of the said case.

Similar construction can be provided for the part of the joint associated to the one or more operating units.

In an embodiment, the mechanical coupling between the two parts of the joint is obtained by means of a low profile mechanical coupling.

According to an embodiment the said low profile mechanical coupling is obtained by providing on the probe in a region coinciding with the distribution of the magnetic elements an indentation having a predefined depth, corresponding to at least part of the height of the socket of the part of the joint supporting the one or more operating units and a predefined shape and dimensions along the external surface of the case of the probe, the socket having a corresponding shape with dimensions equal or slightly smaller as the ones of the indentation.

The said indentation having a depth and the said socket having a height which is smaller than the maximum width of the area occupied by the indentation on the probe case and of the corresponding shape of the socket.

According to a further embodiment which can be provided alternatively or in combination with the previous embodiment, the mechanical coupling may be provided at least in part by centering components provided on the probe at the part of the joint on the probe and on the socket of the part of the joint supporting the one or more operating units, which centering components engage themselves when the two parts of the joint are attached one to the other.

In an embodiment, the centering components comprises two pins or teeth positioned at a predetermined distance one from the other and protruding from the external surface of the probe at the region of the part of the joint on the probe and which pins or teeth engages holes or recesses provided on the socket of the part of the joint supporting the one or more operating units when the two parts of the joint comes in contact one with the other or vice versa According to an embodiment, the said operating unit can be one or more sensors or receivers of a probe tracking system, one or more removable buttons or a small removable keypad bearing one or more buttons or a tool.

According to a further embodiment, when all or at least a part of the one or more operating units cable connection to a system such as for example a probe tracking system, a cable management device is provided which is in the form of a clamping tool of the at least one or more cables of the operating unit or units to the cable of the probe. In this embodiment, the clamping tool can be configured according to the joint for attaching the operating tool to the probe body.

The said clamping tool comprising at least two parts each one mechanically secured to on or part of the cables and which clamping tool parts are engageable one to the other by means of magnetic force and of mechanical coupling.

In this case, according to an embodiment, each clamping tool part is provided with magnetic elements on the side facing the other clamping tool part the said magnetic elements being distributed and polarized in such a way to cause the two parts of the clamping tool to attract each other, the said magnetic elements being distributed over the surface of a layer of magnetic insulating material which covers the side of the clamping tool part designed to come in contact with the other clamping tool part, a mechanical coupling element to one or more cables being provided on the side of the layer of magnetic insulating material opposite to the side of the said layer bearing the magnetic elements so to suppress or reduce the influence of the magnetic field of the magnetic elements on the cables.

As it appears clearly from the above description of the several possible embodiments the combined magnetic and mechanical joint of one or more operating units to the probe can be set in different ways by distributing the main effect of the retention of the operating unit on the probe in different ways on the magnetic force and on the mechanical coupling. Three special cases may be provided which differently weights the magnetic force and the mechanical coupling for the guidance and for the retention effect of the two joint parts:

In a first case the joint is configured in such a way to determine weak magnetic force and strong mechanical retention. The magnetic force is used only as an user guidance when approaching the operating unit joint part to the probe for an easier finding of the correct position in relation to the part of the joint on the probe and the correct way of connection relative orientation of the joint parts one with respect to the other and ready to fit condition of the mechanically performed coupling;

In a second case the magnetic force and the mechanical coupling are set in such a way as to exercise mid magnetic guidance and retention effects and mid mechanical retention effects. The magnetic force is used as an user guidance for an easier finding of the correct way of connection as in the previous case. The connection retaining the operating unit or units on the probe is performed both magnetically and mechanically;

The third case provides a configuration in which a strong magnetic guidance-retention force is exercised and a weak or even absent mechanical retention. In this case, the magnetic force is used as a user-guidance for an easier finding of the correct way of connection as in the two previous cases. The connection is performed mainly/totally magnetically, while the mechanical part, if present, has the sole purpose of indication and/or partially retaining the correct coupling connection between the probe and the operating unit or units, i.e. between the two parts of the joint.

In relation to the further aspects disclosed previously, an ultrasound system is provided comprising a probe and in combination a probe tracking system comprising an electromagnetic field generator configured to generate an electromagnetic field permeating a space in which the probe has to be positioned and at least one sensor or receiver releasably secured to the probe body for measuring the electromagnetic field, a processing unit configured to receive the measured data from the at least one sensor and/or receiver and to determine at least one or a combination of the following parameters comprising position, displacement and/or orientation of the probe, the at least one sensor or receiver being secured to the body of the probe by means of a releasable joint comprising at least two parts one part associated to the probe and one part associated to the sensor or receiver the said two parts of the joint being releasably engageable one with the other by a combination of magnetic force and mechanical coupling.

The above ultrasound system may be provided in combination separately with every one of the previously disclosed embodiments or with all or with any sub combination of the previously disclosed embodiments.

According to a further embodiment, the mechanical parts for releasably attaching the sensor, i.e. the support of the sensor or the support of other operating unit to the probe consist in a seat for the said support of the sensor or of other operating units provided on the probe, the seat having a shape matching the outer peripheral contours of the support and the said seat being opened on one side for engaging and disengaging the said support with and from the said seat, the said seat and optionally the support being provided at least along part of facing surfaces such as a peripheral wall delimiting the opening with mechanical attachment parts of the snap-fit kind.

According to an embodiment, the seat comprises lateral walls and a bottom side formed by the probe wall, the lateral walls delimiting a housing having a shape and dimensions corresponding to the peripheral contours of the support in its condition attached to the probe and overlapping the lateral walls of the support, the lateral walls of the support and the lateral walls of the seat being provided with cooperating parts of the snap fit kind.

According to an embodiment the said parts may be formed by a continuous or discontinuous protrusion of the lateral wall of the seat or by a crown of knobs, both bulging out with a rounded cross section in the direction of the lateral wall of the support, while the support being provided with a continuous or discontinuous groove or with a crown of notches in which the said continuous or discontinuous protrusion or the said crown of knobs snaps.

Alternatively the lateral walls of the seat bears a continuous or discontinuous lip or a crown of teeth at the edge of the lateral wall delimiting the open side of the seat, the said lip or segment of lips or the said teeth being of elastic deformable material and protruding at least at their ends towards the inner zone of the seat in such a measure to allow insertion of the support by elastic broadening of the opening delimited by the said lip, lip segments or teeth while the said lip, lip segments or teeth overlap a peripheral zone of the support along the upper edges of the lateral wall of the said support.

In both the above alternative embodiments of the mechanical coupling parts, according to an embodiment, the said lateral walls of the seat for the support are integrally molded on top of the external surface of the wall of the probe.

In both the above alternative embodiments of the mechanical coupling parts, according to a variant embodiment, the said lateral wall of the seat is formed by the lateral wall delimiting an indentation of the wall of the probe, the height of the said lateral wall of the indentation covering at least part or the entire height of the lateral wall of the support in the condition of the said support engaged in the said seat.

According to a variant embodiment at least part of the height of the lateral wall of the seat is formed by the said lip or segment of lips or the said teeth being of elastic deformable material.

It has to be noticed that the seat and the associated engaging edge is place on the probe at the zone provided with the magnetic elements according to one or more of the preceding embodiments. In an embodiment the said engaging edge surrounds the zone bearing the magnetic elements.

Still according to an embodiment the seat is partly formed by an indentation in the probe wall the bottom wall of the said indentation being provided with the magnetic elements and with the magnetic shield, the said indentation having lateral walls with a height corresponding to part of the height of the support for the sensor and or other operating units to be attached to the probe, while the engaging edge completes the lateral wall of the said indentation to essentially the height of the said support, being attached to the zone of the surface of the probe wall surrounding the said lateral walls of the indentation.

According to a further variant embodiment the said lateral wall of the snap fit seat for the support is formed for its entire height by a lip or a combination of lip segments or a crown of teeth distributed along a line enclosing the zone of the wall of the probe being provided with the magnetic elements and with the magnetic shield, the said lip, or the said combination of lip segments or the said crown of teeth being molded on the outer surface of the probe wall.

According to a further embodiment, at least two different operating units may be attached in a releasable way to the probe, each operating unit being provided with an own support, and the probe being provided with a snap fit seat for each of the said support placed in different zones.

A variant embodiment in which at least two different operating units may be attached in a releasable way to the probe, each operating unit being provided with an own support, each support or at least part of the said supports being provided on the side opposite the side facing the seat on the probe with a seat for the support of the further operating unit of the said at least two operating units.

According to an embodiment the said snap-fit seats on the support of at least part of the said at least two operating units are configured according to one of the above disclosed variants and particularly are provided with a combination of a magnetic coupling and of a mechanic coupling the magnetic coupling being configured according to one of the previously disclosed embodiments and the mechanical coupling being also configured according to one of the previously disclosed embodiments.

This last embodiment in which the support of at least some of the operating units is provided with magnetic and mechanical coupling for the support of a further operating unit allows to attach the supports of different operating units one on top of the other. A specific embodiment provides for a combination of a probe, a keyboard and a sensor attached in a releasable way to the probe, the sensor having a support and the keypad having a support in the form of an attachment pad, the attachment pad of the keyboard being provided on the side facing the probe with a seat for releasably coupling the support of the sensor thereto.

The magnetic guidance of the Fusion Imaging sensor support is an important resource especially in cases where the probe is used with the (sterile) protective cover. In this case, when the Fusion Imaging sensor has to be attached once the probe has been already placed within the cover, the magnetic guidance drives the operator to correctly find the attachment spot as well as guiding to the correct attachment direction/position. The mechanical attachment securely connects the Fusion Imaging sensor support to the probe body. The same considerations are still value also regarding the option of a full magnetic attachment of the Fusion Imaging sensor to the probe body.

BRIEF DESCRIPTION OF THE DRAWINGS

FIGS. 11, 12 and 13 show a further embodiment of the combination of probe and a sensor of a tracking system of the probe the embodiment further comprising means for managing the cable of the sensor.

Although the following example is directed to an ultrasound probe combined with a sensor of a tracking system of the probe and with a touch key pad comprising one or more buttons to control functions of the tracking system and/or of the ultrasound system, the basic idea of the disclosed embodiments can be easily extended to other operating units to be combined with the probe and/or for example with surgical tools to be used in combination with the probe.

FIGS. 19, 20, 21, 22, 23, 24 and 25 show different alternative embodiments of the mechanical snap-fit coupling of the support of one or more operating units to a probe, in the Figures the magnetic coupling not being shown in detail while being considered provided according to one or more of the embodiments disclosed in the previous Figures and in the corresponding description.

Figure 1:
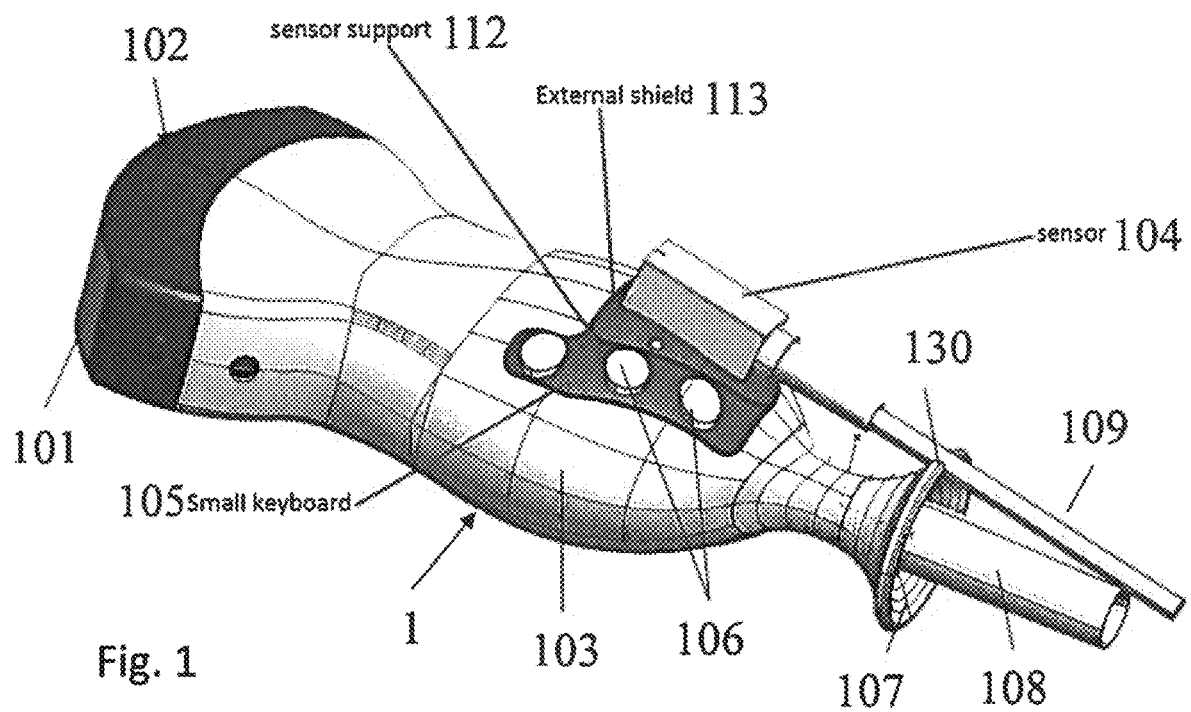
FIG. 1 shows a perspective view of an embodiment in which to the handle portion of the case of an ultrasound probe there are releasably secured a keypad and a sensor of an electromagnetic tracking system.

FIG. 1 shows one example of an ultrasound probe 1. The probe 1 comprises a probe body formed by a case. The case comprises a shell generally of plastic material which forms the housing for the ultrasound transducer array which is provided at a ultrasound transmit and receive window 101 in the probe head 102. The probe has a handle portion 103 with a flattened cross section such as an ellipsoidal or oval cross section having a major and a minor diameter.

In the disclosed example, the at least one of the sides of the handle portion 103 parallel to the major diameter of the said cross section is destined to bear a sensor 104 of a probe tracking system and in combination therewith a small keyboard 105 comprising one or more buttons 106. In the disclosed embodiment, the buttons are provided in the number of three.

At the side, opposite to the transmit and receive head 102 the case of the probe has a cable exit 107 for the cable 108 connecting the probe receiving and transmission channels to the transmit and receive channels of an ultrasound system.

The sensor 104 is also provided with a cable 109 for transmitting the signals measured by the sensor 104 to a processing unit of a tracking system disclosed in the following.

According to an embodiment, the cable exit 107 widens in a funnel like manner at its end and is provided with a slot 130 for releasably retaining and guiding the cable 109 of the sensor 104 in such a way to be parallel or essentially parallel to the cable 108 of the probe.

Also, the keyboard 105 can be provided with a cable which is not shown in the present example. In a variant embodiment which is the one shown, the keyboard 105 is provided with a wireless transmit/receive unit for communicating wirelessly with a transmit/receive unit of one or more processing units such as for example with the control board of the ultrasound system or with the control unit of a tracking system. Other systems may be provided in combination with the ultrasound system and the probe which may be controlled by one or more buttons 106 of the keyboard and which might be dedicated to carrying out other additional functions in combination with the ultrasound imaging and the probe tracking function.

In the above case, a transmit and receiving unit of the signals generated by the keyboard can be provided which is configured to operate as an intermediate communication interface of the keyboard with each one of the one or more systems by channeling each button to one or more systems according to the functions controlled by the said button, so that the same keyboard can be operated alternatively in combination of only one different system provided in combination or with two or more systems.

As it will be disclosed later in the description there may be provided also a joint for coupling each other the different cables 108 and 109 at least at one point of their length and which can be configured with a similar structural concept as the joint releasably securing the sensor 104, the keyboard 105 or the other operating units to the probe body.

Figure 2:
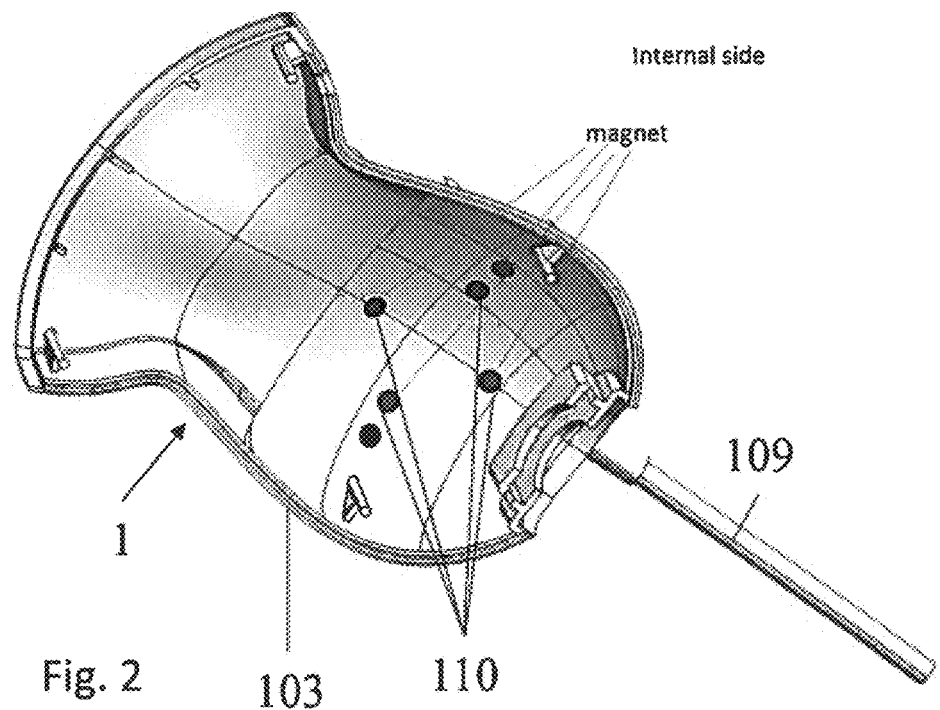
FIG. 2 shows a perspective view of the half shell forming the case and the handle portion of a probe according to FIG. 1, on the side facing the interior of the probe a predefined number of magnetic elements being bonded to the wall of the probe and being distributes according to a certain distribution pattern.
Figure 3:
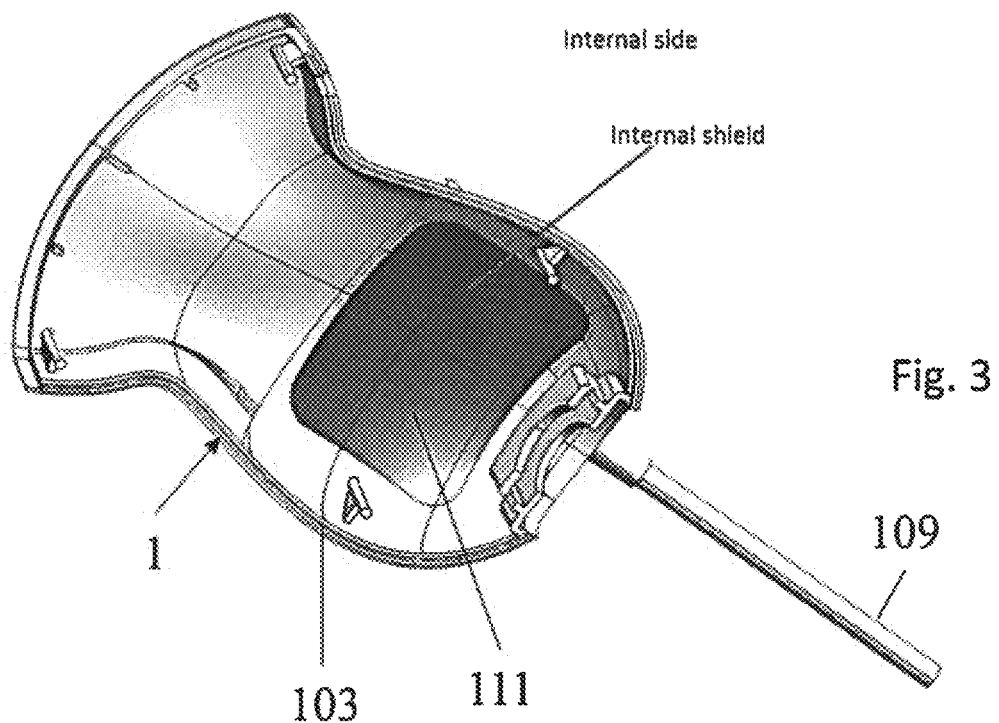
FIG. 3 shows a perspective view of the half shell forming the case and the handle portion of a probe according to FIG. 1, on the side facing the interior of the probe in a following step of the construction in which the pattern of magnetic elements is further covered on the side facing the inside of the probe with a magnetic shield.

According to an embodiment shown in the FIGS. 1, 2 and 3 the sensor 104 and the keyboard 105 are secured to the probe body by a combination of magnetic force and mechanical coupling.

In the above embodiment, a releasable joint is provided between the sensor and the probe body which joint is formed by two parts releasably engageable together magnetically and mechanically each one of the said part of the joint being associated with the probe or with the sensor.

FIGS. 2 and 3 show an embodiment in which the joint part associated with the probe case, and particularly to the handle portion 103 is formed by the wall of the shell forming the handle portion of the case, normally of plastic material, one or more magnet elements or seeds 110 distributed in a predetermined number and according to a predetermined pattern along the said wall and a layer 111 of magnetic insulating material which covers towards the inside of the probe shell the entire region where the magnetic elements 110 are positioned according to the said predetermined pattern of distribution.

Several different ways of bonding the magnetic elements and/or the magnetic insulating layer may be provided, for example such as co-molding with the probe case or by over-molding of the case on the layer of magnetic insulating material and on the magnetic elements or by co-molding or over-molding the probe case to or on the magnetic elements and the following over molding or laminating the layer of magnetic insulating material on the inside surface of the wall forming the shell of the probe case over the region bearing the magnetic elements pattern.

Figure 5:
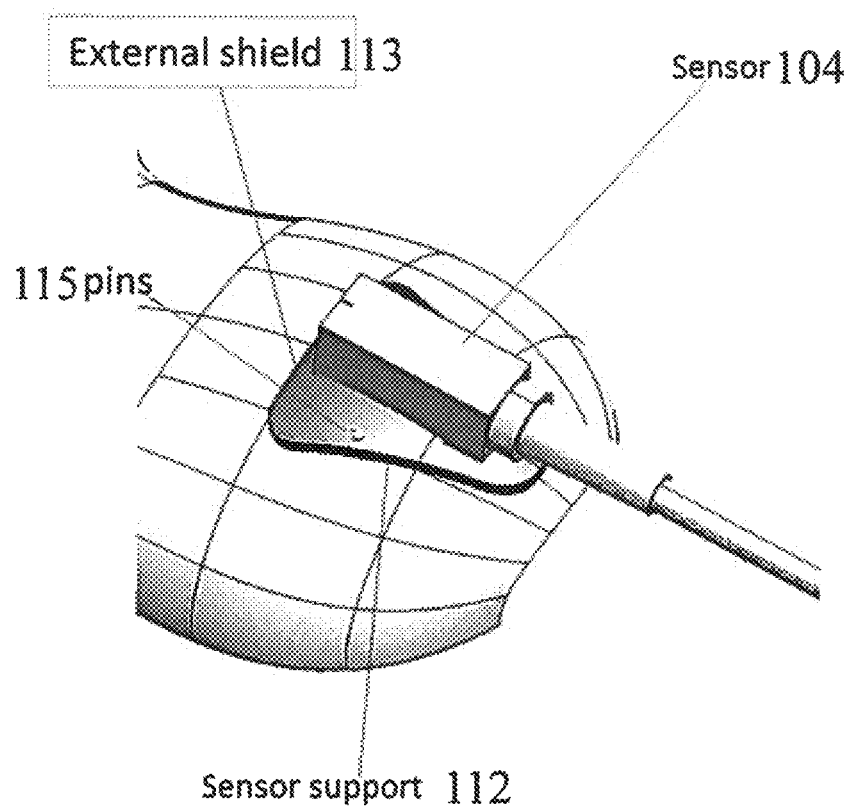
FIG. 5 shows a first variant embodiment of the joint part supporting the sensor and in the condition coupled to the joint part on the probe.
Figure 6:
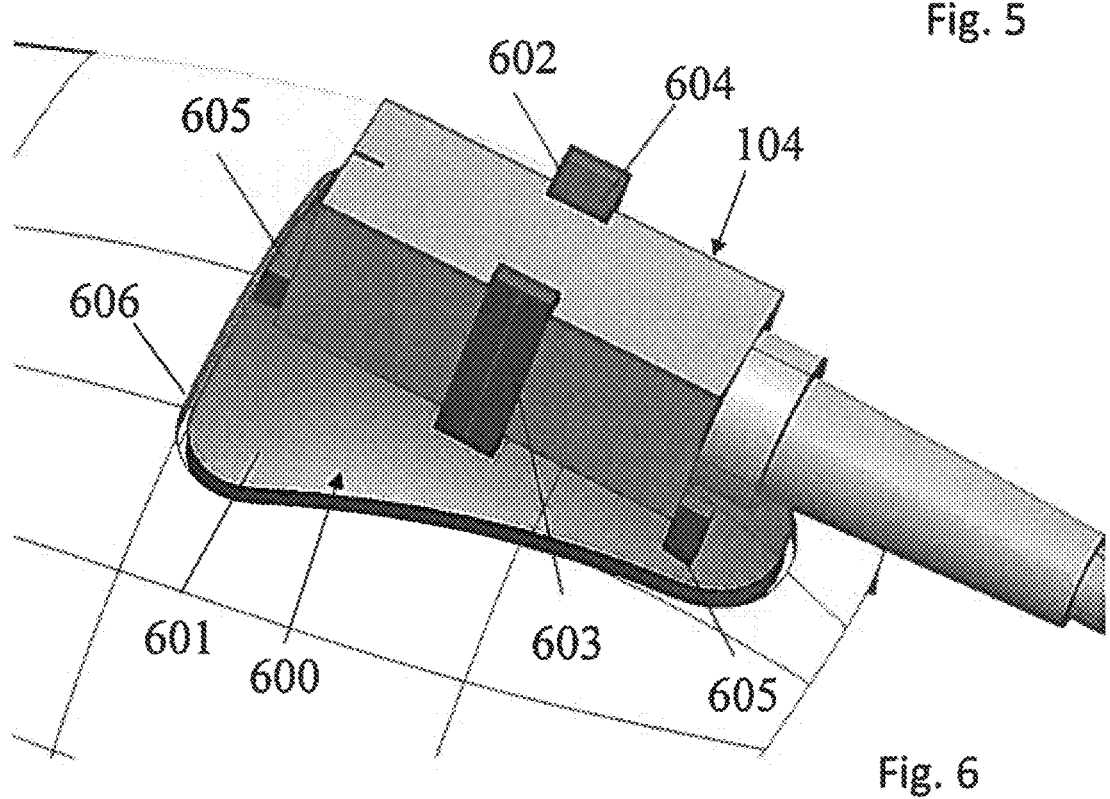
FIG. 6 shows a variant embodiment of the joint part on the probe and the joint part of the sensor.

According to an embodiment shown particularly in FIGS. 1, 5 and 6, the sensor 104 is secured in a releasably or in a steady, i.e. non-releasably way to a sensor support 112, which comprises and external shield 113 of magnetic insulating material on the side facing the sensor and magnetic elements (not shown in detail) on the side of the external shield 113 facing the joint part on the probe, i.e. the region of the probe case bearing the pattern of magnetic elements 110.

The magnetic elements on the joint part associated to the sensor 104 are provided with a pattern of distribution along the surface of the support for the sensor 104 and with a polarization such as to generate an attraction force between the said support and the region of the probe case, and particularly the probe handle portion at which the pattern of magnetic elements 110 is provided on the said probe.

Different variant embodiments may be provided considering the configurations of the pattern of distribution of the magnetic elements 110 on the probe and on the support for the sensor 104 which patterns might be identical and congruent so that each magnetic element on the probe coincide with each magnetic element on the support, the polarization of the magnetic elements being such the magnetic elements on the probe and on the support faces themselves with opposite polarized poles for generating the attraction force.

A variant embodiment may provide for different pattern on the probe and on the support in order, for example, to enhance a guiding action of the support relatively to the probe for bringing the two parts of the joint in the correct mutual engagement position. The polarization of the magnetic elements on the probe and on the support for the sensor being such that an attraction force is generated between the said probe and the said support.

According to a further embodiment, which is shown in FIG. 6, the support 600 for the sensor comprising the magnetically insulating shield 601 is further releasably mechanically coupled to the sensor 104. In this embodiment, the support 600 is provided with at least two opposite elastic deflectable wings 603 which can be elastically divaricated relatively one from the other and which are provided with at least an end tooth 602 for superimposing to an external surface of the body of the sensor 104. According to an improvement each tooth has a wedged cross section in a direction of the longitudinal axis of the wings 603, the inclined surface 604 of the wedged cross section being oriented such that its starts at the tip of the wing 603 and is directed towards the opposite wing 603 in direction of the root of the corresponding wing such as to form deflection surface cooperating with the body or the sensor 104. When pressing the body of the sensor 104 against the teeth 602 in the direction of engagement of the sensor 104 with the support 600, the wings are automatically divaricated allowing the sensor to be brought in snap engagement between the two wings and between the facing side of the shield 601 of the support 600 and the retaining teeth 602 of the wings 603.

The above describe configuration is only one of the possible alternatives of releasable snap engagement of the sensor 104 with the support 600, i.e. with the joint part associated to the sensor 104.

According to a further feature, the support 600 may also be provided with centering guides of the sensor relatively to the support and particularly to the magnetic shield 601 of the support. This centering guides can be steps or protrusions 605 on the support surface facing the sensor 104 defining at least parts of the external perimeter of the body of the sensor 104 and having the function of positioning stops superimposing at least some of the lateral sides of the body of the sensor or part thereof, particularly of the lateral sides not parallel to the wings 603 and thus blocking the sensor in relation to displacement in a direction perpendicular to an axis or a plane connecting the wings 603.

In relation to the above shown embodiment it has to be noticed that without any limitation to the provision on the same support 600 or on different supports of two or more sensors 104, only one single electromagnetic sensor 104, properly set and fine-tuned, enables high levels of precision (from 0 to 5 mm) reducing at the minimum the ergonomics problem of the management and manipulation of the probe and the related weight/ergonomics changes is preferable with respect to any other solution which considers two or more tracking sensors which is in any case also contemplated as alternative embodiment.

According to an embodiment the part of the joint on the probe and/or the part of the joint associated with the sensor or to one or more sensor or other operative units or to a combination of different operative units there are provided three magnetic elements positioned at three different points. These three points are positioned respectively each one at a vertex of a triangle preferably at the vertex of an isosceles triangle whose symmetry axis is oriented parallel to the central symmetry axis of the probe passing through the transmit and receive window 101 and with the vertex falling on the said symmetry axis facing the exit of the probe case for the cable opposite to the said transmit and receive window 101.

Figure 4:
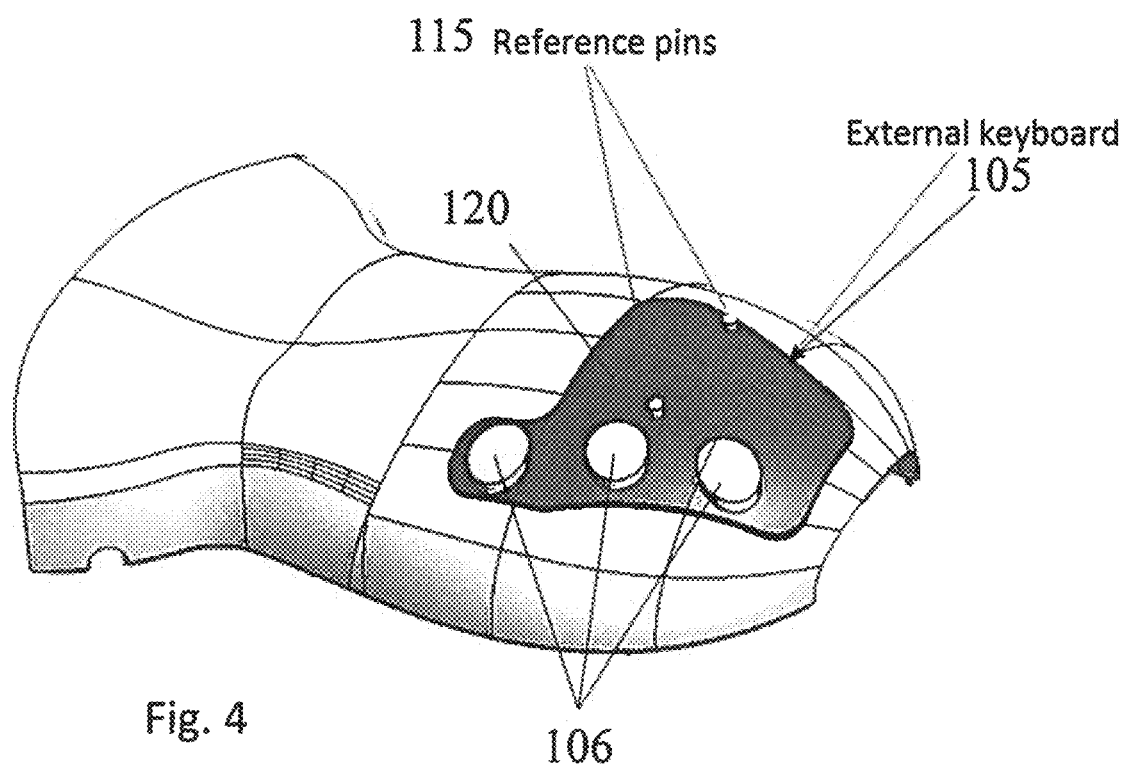
FIG. 4 shows a perspective view of the half shell forming the case and the handle portion of a probe according to the preceding FIGS. 1-3, on the external side of the probe and a keypad being attached to the said external surface of the probe body.

According to the embodiment shown in FIGS. 1, 4 and 5, in combination with the connection by magnetic force between the two parts of the joint for securing the sensor 104 to the probe body or case and in the present embodiment preferably to the handle portion 103 of the probe also a mechanical coupling is provided between the said two parts of the joint.

The mechanical coupling may be low profile as the one disclosed in the embodiment of FIGS. 1, 4 and 5. Here the mechanical coupling has merely the function of ensuring that the two parts of the joint associated respectively to the probe and to the sensor, i.e. the region of the probe case where the magnetic elements 110 are positioned and the cooperating support 112 of the sensor, are positioned correctly one with respect to the other and that this relative position is safely maintained during operation of the probe, avoiding relative displacements along the probe surface. The force retaining the support of the sensor in a condition adhering against the probe case is in this case mainly the magnetic force. Thus, a magnetic force vector is oriented essentially perpendicularly to the surface of the case of the probe, or essentially in a direction incident relatively to the said surface of the case of the probe, while the mechanical coupling is blocking the support in relation to forces having a direction essentially parallel or tangent to the said surface of the case of the probe at the corresponding joint part. In this embodiment, the support 112 and in the specific example also the magnetic shield is provided on opposite sides of the sensor with at least a passing hole, while two reference pins 115 protrude from the external surface of the case of the probe which pins are positioned with a predetermined position relation to the distribution pattern of the magnetic elements 110 on the probe and each one coinciding with one of the passing holes on the support 112 of the sensor 104.

FIG. 6 shows a variant embodiment of the low profile mechanical coupling between the two parts of the joint associated respectively to the case of the probe and to the support of the sensor. In this embodiment, the pattern of magnetic elements 110 on the probe is positioned at least for a part, preferably for all the magnetic elements 110 coinciding with the part of the wall of the probe case forming the bottom wall of an indentation 606. The indentation 606 having an open side with dimensions and shape of its aerial projection which is corresponding to the shape of the aerial projection and the dimensions of the support 600 of the sensor. The dimensions of the indentation 606 can be a little greater than the dimensions of the support 600 in a measure sufficient to ensure to the support to engage properly the indentation coming in contact with the bottom side of it. The depth of the indentation may be at least a fraction of the thickness of the support 600 or even equal or bigger than the said thickness. Also in this case, the mechanical coupling ensures the maintenance of the correct relative positioning of the two parts of the joint securing the sensor to the probe, namely of the region provided with at least a part of the magnetic elements 110 on the probe and the support 600 and the magnetic elements provided on it. Thus, the displacement of the support 600 along the probe body is not possible ensuring always a correct relative positioning of the sensor on the probe. The retention of the sensor against the case of the probe against a detachment from the said case is obtained merely by the magnetic force as also the guidance of the support against the indention and the correct positioning of the support shape relatively to the indention.

In this case the polarization of the magnetic elements on the probe and thus of the corresponding magnetic elements on the support may be different for the magnetic elements in different zones of an alignment axis so to cause a repulsive magnetic force if the support is wrongly oriented for example of 180° with respect to the probe. This is particularly useful in a condition in which the sterile wrapping of the probe renders difficult to understand the position and shape of the indentation. When the alignment of probe and support is correct, the usual guiding attractive magnetic force is generated between sensor and probe so as to allow the support to be correctly positioned in engagement with the indentation.

The above variants of the mechanical coupling may be provided in combination one with the other, for example providing the pins protruding from the bottom side of the indentation and thus enhancing the mechanical coupling between prove and support, i.e. sensor.

According to a further embodiment, illustrated in FIGS. 1 and 4, together with the sensor 104, on the case of the probe a small keyboard 105 is provided with one or more buttons 106 that may be secured releasably to the case body.

According to a first embodiment shown in FIGS. 1 and 4, the keyboard is mechanically coupled to the joint part on the probe, while it is retained attached to the probe by the magnetic force between the part of the joint on the probe and the part of the joint associated with the sensor, i.e., the support 112, forming an intermediate layer between the two parts of the joint. According to this embodiment as can be appreciated from FIGS. 1 and 4, the keyboard is provided on a pad 120 of flexible and/or pliable material such as for example silicone or rubber or other materials with similar flexibility and/or pliability. The pad 120 is provided with a passing hole for each or at least some of the reference pins protruding from the surface of the case of the probe and which pins 115 all or at least some of them engages also the passing holes on the support 112 of the sensor.

According to a further embodiment not shown in the Figures, the keyboard 105 may be provided optionally or alternatively to the mechanical coupling with magnetic elements cooperating with the magnetic elements or with at least some of the magnetic elements bonded to the probe case, similarly to the support 112 for the sensor 104 which magnetic elements 110 on the case of the probe may be partly the same for the pad 120 and for the support 112 of further magnetic elements destined to cooperate only with coinciding magnetic elements of the keyboard. In this case, at the positions of the said magnetic elements the pad 120 may be provided on the side opposite to the inside of the probe with a magnetic shielding layer and the layer in the inside of the case for insulating the magnetic field may be extended to the said further magnetic elements (not shown in the Figures).

A keyboard as in the embodiment of FIGS. 1 and 4 may also be provided in the embodiment of the FIG. 6. Here the indentation may be provided with a greater depth and the pad of the keyboard may form in a position coincident with the indentation on the probe case also an indentation which is shaped and dimensioned in a manner allowing the support 112 to be inserted and housed therein at least for part of its thickness providing a mechanical low profile coupling for the pad and for the support 112 of the sensor 104 and causing the keyboard to be retained in the attached position in the indentation of the probe by the magnetic attraction between support 112 and magnetic elements 110 on the probe.

Also for this embodiment it is possible to provide further magnetic elements 110 on the probe which are destined to cooperate in an attractive manner with coinciding magnetic elements of the keyboard according to every of the variants disclosed in relation to the previous embodiment.

According to a further variant embodiment, the keyboard may be mechanically coupled to the exterior side of the support 112 in a similar way as the sensor 104 in the embodiment of FIG. 6.

Figure 7:
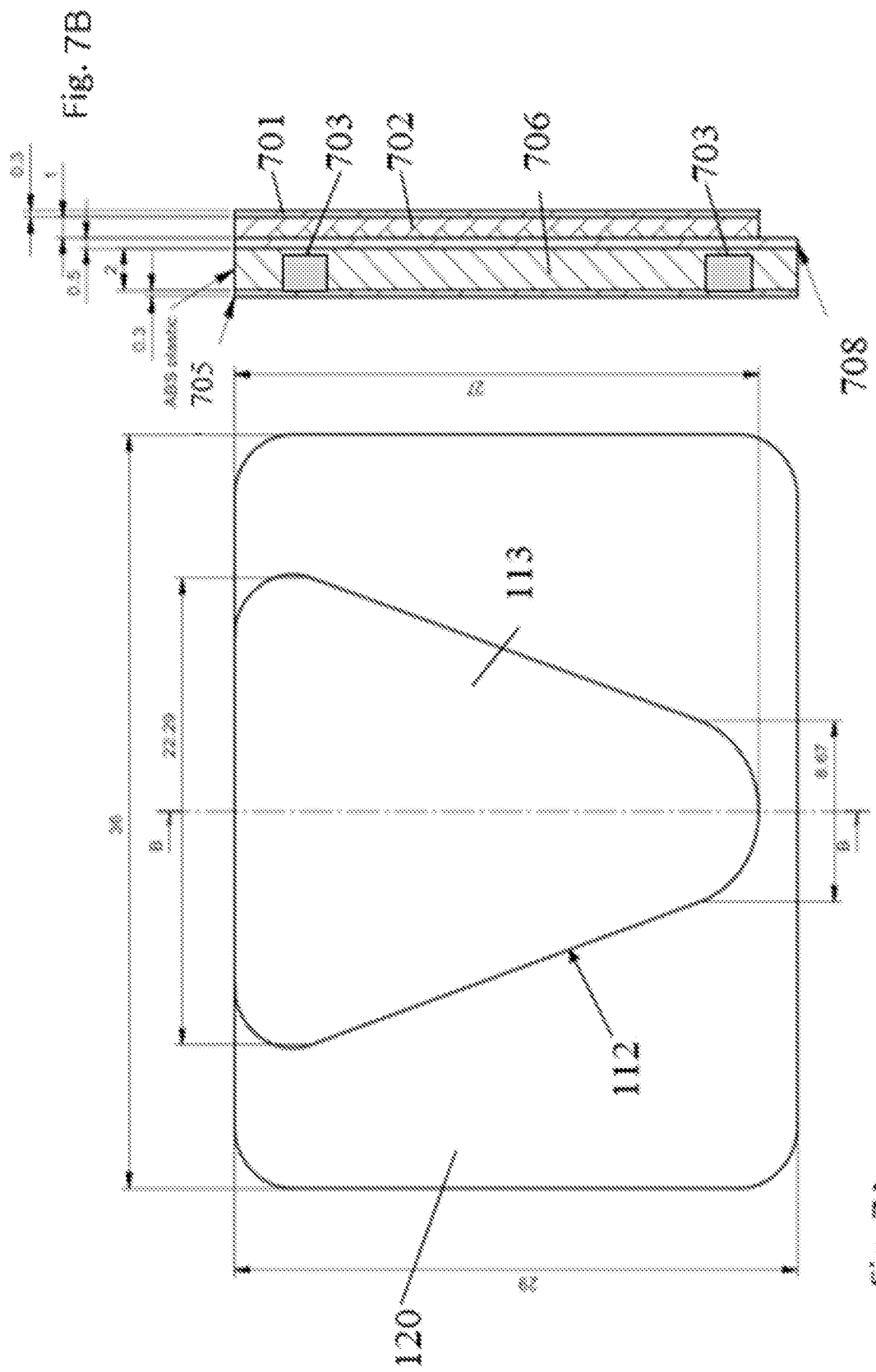
FIGS. 7a and 7b show a further variant of the joint fore releasably attaching the sensor to the probe body.

FIGS. 7a, 7b show two views of an embodiment of the joint between a sensor 104 and the wall of the case of the probe, particularly at the region of the handle portion.

FIG. 7a shows an aerial projection of the pad 120 of the keyboard and of the magnetic shield 113 on the support of the sensor, their geometric shapes and their relative positions when the support is secured to the probe.

FIG. 7b is a cross sectional view showing the layer configuration of an embodiment of the joint in the condition in which the two joint parts and the keyboard are secured together. Starting from the outside the support 112 is provided with a magnetic shield 701 which coincides with a layer 702 of permanently magnetized material cooperating with the one or more magnetic elements 703 bonded or integrated in the material of the wall 706 of the case of the probe. A magnetic shielding layer 705 being laminated onto the internal side of the wall of the case of the probe covering the entire area on which the magnetic elements 703 are distributed along the wall of the case of the probe and the entire area of the magnetized layer 702 on the sensor support. Optionally between the magnetized layer 702 on the sensor support and the external surface of the wall of the case of the probe a pad 708 of a keyboard is interposed.

According to an embodiment, the magnetic shield and the layer of magnetic insulating material are formed by so called mu-metal or other high permeability materials having similar features. Mu-metal is a nickel—iron soft ferromagnetic alloy with very high permeability, which is used for shielding sensitive electronic equipment against static or low-frequency magnetic fields. It has several compositions. One such composition is approximately 77% nickel, 16% iron, 5% copper and 2% chromium or molybdenum. More recently, mu-metal is considered to be ASTM A753 Alloy 4 and is composed of approximately 80% nickel, 5% molybdenum, small amounts of various other elements such as silicon, and the remaining 12 to 15% iron. Mu-metal typically has relative permeability values of 80,000-100,000 compared to several thousand for ordinary steel. It is a "soft" ferromagnetic material; it has low magnetic anisotropy and magnetostriction, conferring a low coercivity so that it saturates at low magnetic fields. Other high-permeability nickel—iron alloys such as permalloy have similar magnetic properties; mu-metal's advantage is that it is more ductile and workable, allowing it to be easily formed into the thin sheets needed for magnetic shields. Other materials with similar magnetic properties include Co-Netic, supermalloy, supermumetal, nilomag, sanbold, molybdenum permalloy, Sendust, M-1040, Hipernom, HyMu-80 and Amumetal. In an embodiment, the plastic material of the case of the probe can be ABS plastic or other similar plastic.

In an embodiment, the magnetized layer of the support of the sensor can be of magnetic rubber and is polarized in such a way as to generate attractive forces in cooperation with the magnetic elements 703 integrated or bonded to the wall 706 of the case which can be also magnetic silicon rubber.

In an embodiment, similarly the pad 708 of the keyboard can be also made of a layer of magnetic rubber such as magnetic silicon.

A variant embodiment may provide as already disclosed above a pad of the keyboard which is of a-magnetic material instead that magnetic material.

As magnetic materials, different materials can be used examples of which are plastic ferrite or plastic neodymium.

According to a further feature, the concept of the joint between probe and sensor of one or more other kinds of operating units can be also applied for joints between the cable of the probe and the cable or cables of one or more of the operating units associated with the probe. Thanks to this provision the manipulation of the probe during use in combination with one or more operating units secured to the probe such that at least a sensor of a probe tracking system and/or at least a keyboard with one or more control buttons and/or other kind of operating units is dramatically facilitated by managing the cable of the probe and the one or more further cables in such a way that the cables are held together at least for a certain length from the probe avoiding interferences of each cable with the probe during use.

FIGS. 11, 12 and 13 show an embodiment of the combination of an ultrasound probe and a sensor 104 or other operating unit, the probe 1 and the sensor 104 being releasably attached one to the other with a joint which is configured according to one or more of the previously disclosed embodiments and variants and the sensor 104 being provided with a cable for transmitting the measured signals to a processing unit of a tracking system or other kinds of operating system combined with an ultrasound imaging system.

The support of the sensor 1101 in FIG. 11 has a different shape of its aerial projection. The end 1104 of the case 1102 of the probe from which the cable 1103 of the probe exits has a longitudinal slot 1105 in which the cable 1106 of the sensor 1101 can be engaged and guided parallel to the cable 1103 of the probe. The slot 1105 can be provided in the end of the case of the probe or in a part 1108 forming a sort of sealing terminal of the opening for the cable 1103 of the probe and being fixed to the said opening while it is provided with a hole for passing the cable 1103 of the probe and with the peripheral slot 1105 oriented parallel and optionally coincident with the said hole for the cable of the probe.

At a certain distance from the said end of the case of the probe, the cable 1103 and the cable 1106 of the sensor 1101 are held releasably together in an essentially parallel relative position by a releasable joint. The releasable joint 1108 is shown with greater detail in FIG. 13. Along the cable 1106 of the sensor is provided for a segment of a certain length and at least in one or more points of the length of the said cable 1106 with a part of a joint in the form of a small hose 1301 having a predetermined length and diameter. The hose 1301 is formed by at least two layers, one layer of magnetic shielding material which is laid directly on the peripheral outside surface of the cable 1106 and a layer of magnetized material or a layer incorporating magnetic elements which is superimposed on the said layer of insulating material.

The said hose 1301 being destined to engage a longitudinal slot 1303 of the retaining element 1302 which is attached to the cable 1103 of the probe. The said retaining element can be similarly in the form of a hose enveloping at least partially the cable 1103 of the probe and has a longitudinal slot with a cross section corresponding to the cross section of the hose 1301 on the cable 1106 of the sensor. The said longitudinal slot being provided with a magnetized layer or with a pattern of magnetic elements on its outer surface which is bonded to the retention element 1302 by means of an intermediate layer of magnetic insulating material. The layer of magnetic insulating material avoids that the magnetic field of the magnetized layers or of the magnetic elements propagates in the cables and generate electromagnetic disturbing the signals.

As it appears from FIG. 11 more than one joint for coupling together the cable of the probe to the cable of the sensor can be provided and distributed along the length of the said cables at predefined intervals and covering preferably and at least a length that displaces the point at which the cables are separated one from the other away from the region within which the cable interferes with the zone of displacement and manipulation of the probe.

Figure 14:
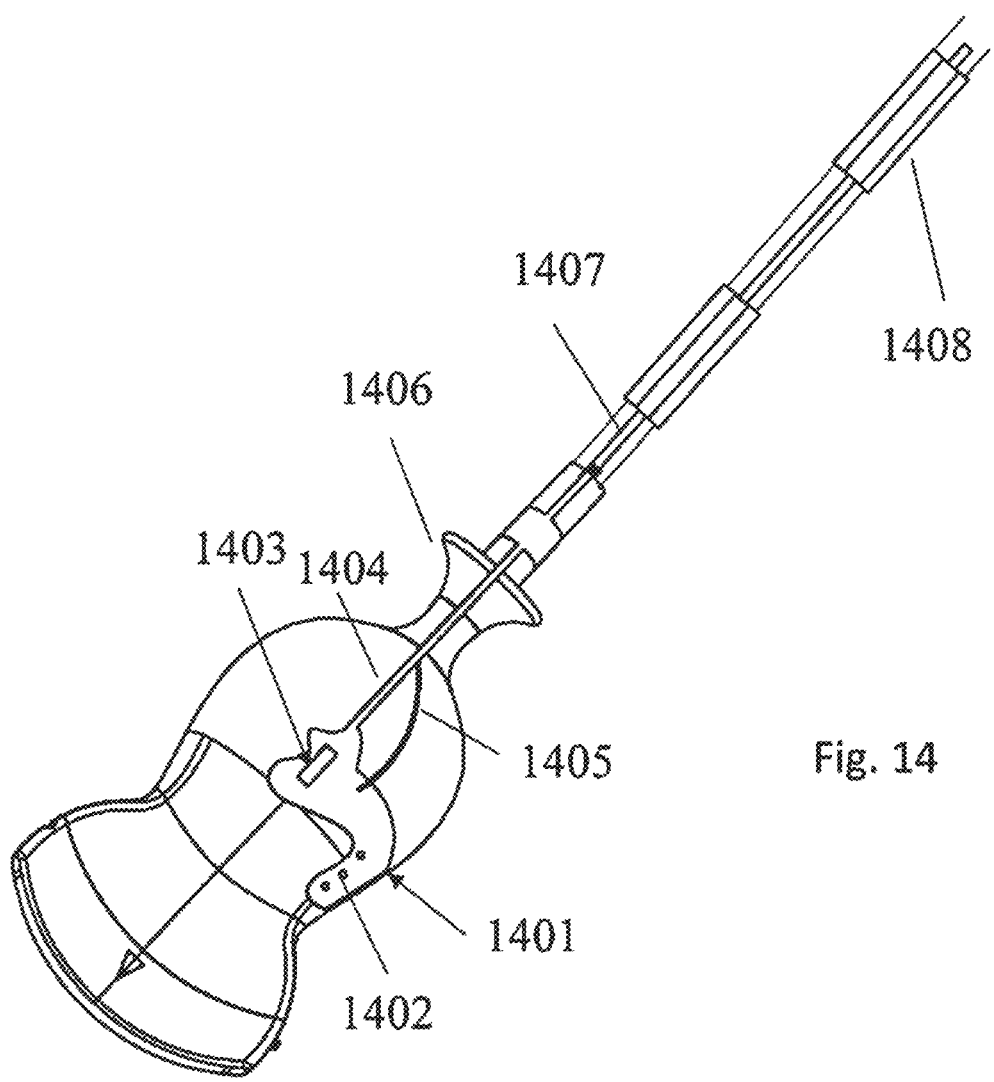
FIGS. 14, 15, 16, 17 and 18 show different views and details of the further embodiment of the combination of a probe a sensor of a probe tracking system and a keyboard to be attached to the probe and further comprising means for guiding the cables of the sensor and of the keyboard along the cable of the probe.
Figure 15:
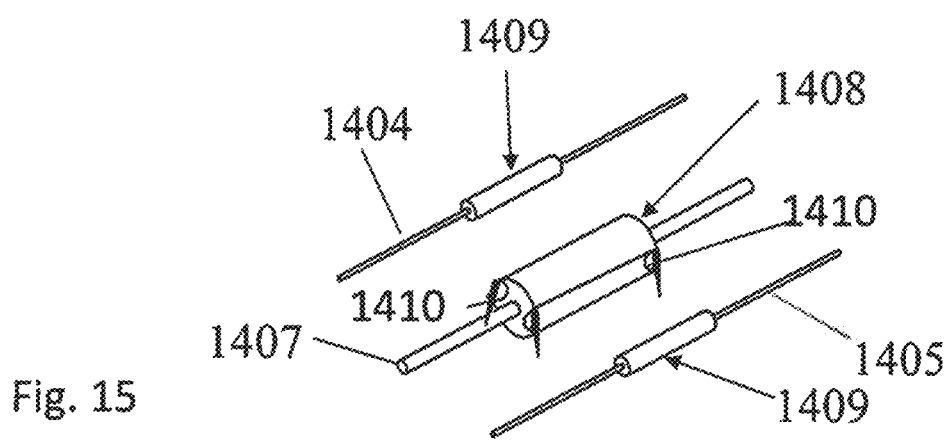
Figure 16:
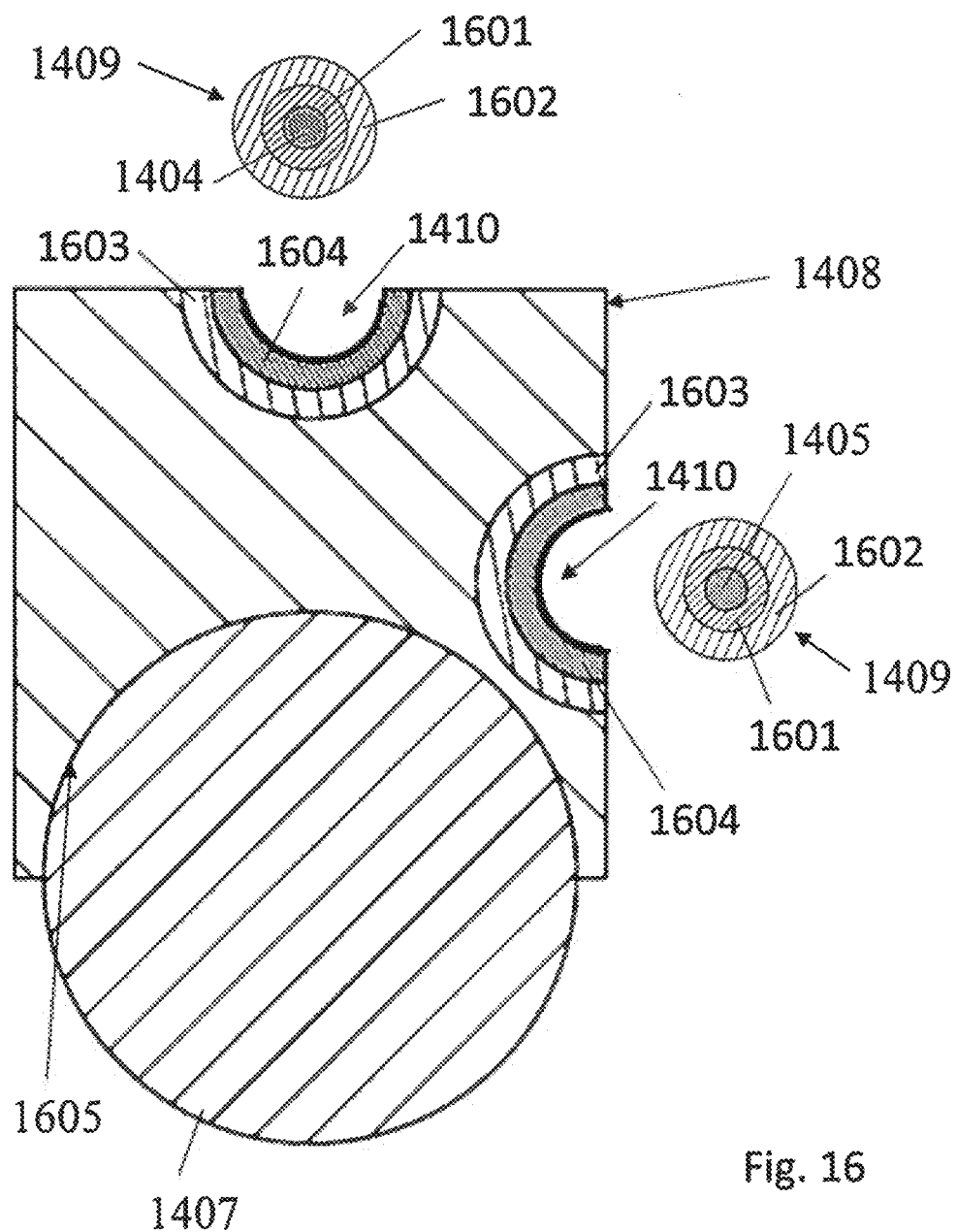

FIGS. 14, 15 and 16 show a variant embodiment which is a combination of the embodiment in which the probe is combined with a keyboard 1401 with buttons 1402 and with a sensor 1403 each having a dedicated cable 1404 and 1405 with the embodiment of FIGS. 11 to 13.

A terminal part 1406 of the probe body at the exit of the cable 1407 from the probe is configured according to the embodiment of FIGS. 11 and 12. The longitudinal slot in the terminal part 1406 is dimensioned such that both cables of the sensor and of the keyboard fit therein. Along the cable of the probe at predetermined distances one from the other one are more retention elements 1408 for releasably attaching the cables 1404 and 1405 of the sensor and of the keyboard. According to this embodiment the said retaining elements 1408 are in principle configured according to the one described with reference to the embodiment of FIGS. 11 to 13 but instead of having only one longitudinal slot for releasably engaging the hose of one cable, each cable 1404 and 1405 has its own retention hose 1409 positioned coinciding with each one of the retention elements 1408 on the cable of the probe and with each one engaging a dedicated longitudinal slot 1410 on the corresponding retention element 1408. Thus, in this embodiment, as shown in FIG. 15, the retention element 1408 has two longitudinal slots positioned at different angular positions in relation to the axis of the cable of the probe, preferably such that each cable 1404 and 1405 is attached at one of the two opposite sides of the cable of the probe each longitudinal slot 1410 being destined to engage the retention hose 1409 of one of the two cables 1404, 1405. As a result, the cables 1404 and 1405 are properly guided each one along a side of the cable of the probe.

In the embodiment, according to FIGS. 15 and 16 the longitudinal slots on the retaining element 1408, the retaining hoses 1409 for the cables 1404 and 1405 and the probe cable are shown in cross section according to a plane perpendicular to the axis of the said cables.

As a variant from the previously described position of the two longitudinal hoses 1410 it appears that these two hoses 1410 are angularly spaced by an angle of 90° around the axis of the cable 1407 of the probe.

According to a further feature the retaining hoses 1409 enveloping the cables 1404 and 1405 of the sensor and of the keyboard have a circular cross-section and the longitudinal slots 1410 are a corresponding circular cross section with an essentially identical radius and with an angular extension of maximum 180° around the central longitudinal axis of the slots.

Furthermore FIG. 16 shows the above already disclosed layer configuration of the longitudinal slots on the retaining elements and of the retaining hoses on the cables of the sensor and of the keyboard. The retaining hoses 1409 for the cables 1404 and 1405 each comprises a first layer 1601 directly enveloping the cables and being of a magnetic shielding material and a layer 1602 of magnetized material or incorporating magnetic elements covering towards the outside the layer 1601 of magnetic shielding material.

In an analogous way the longitudinal slots 1410 are covered towards the outside first by a layer of magnetic shielding material 1603 which is covered towards the outside by a layer 1604 of magnetized material or a layer incorporating magnetic elements.

Each retaining element 1408 can be attached to the cable 1407 of the probe by a releasable mechanical coupling or by chemical physical bonding or using a joint configured according to the embodiment described herein for the cables 1404 and 1405. In FIG. 16 a slot 1605 having half-cylindrical form houses the cable 1407 of the probe in which the said cable can be retained by mechanical coupling for example by one or more bands distributed along the length of the semi-cylindrical slot and which are secured on one side to one edge of the slot and are wrenched against the cable by means of an engaging head secured to the opposite edge of the slot.

Figure 17:
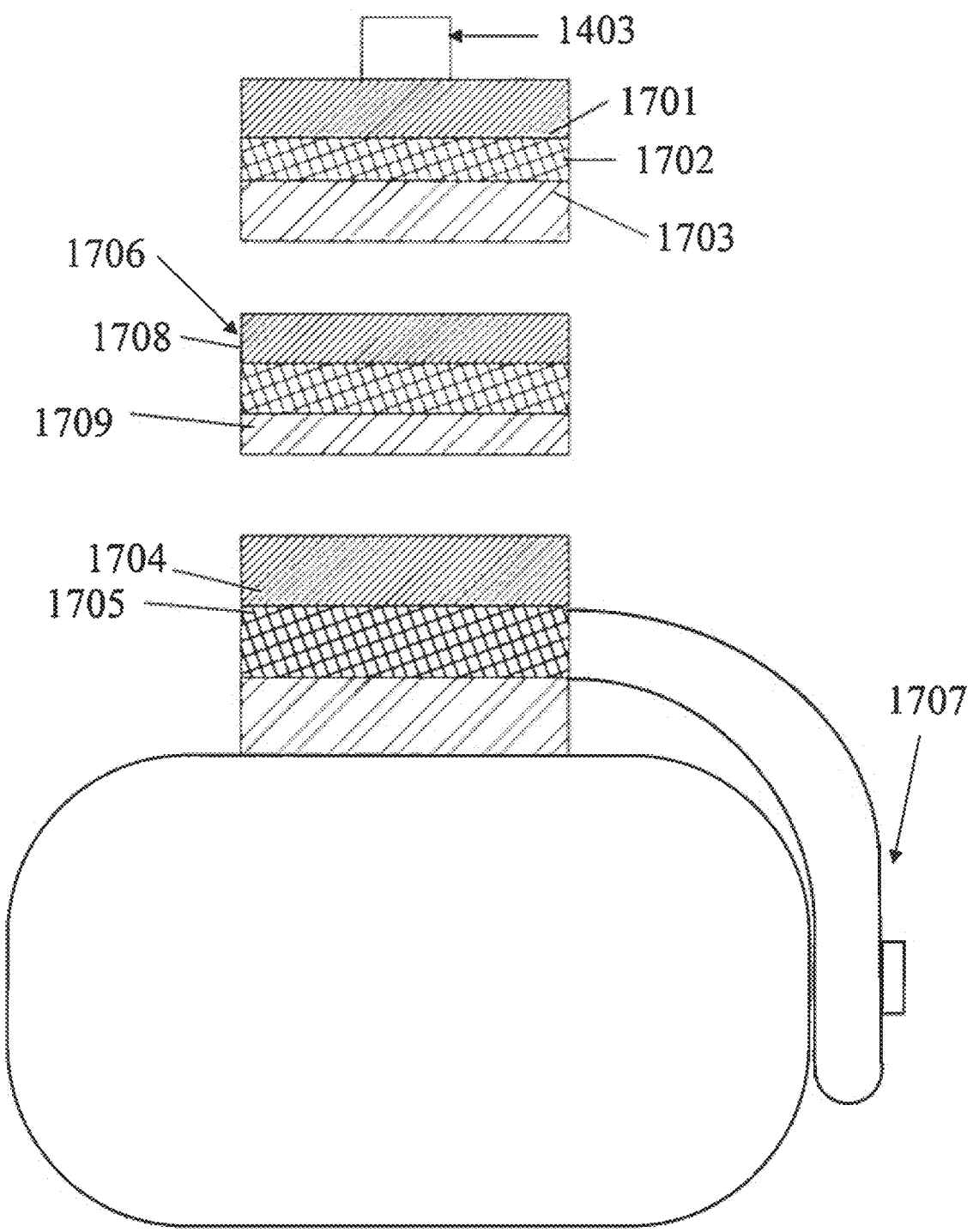
Figure 18:
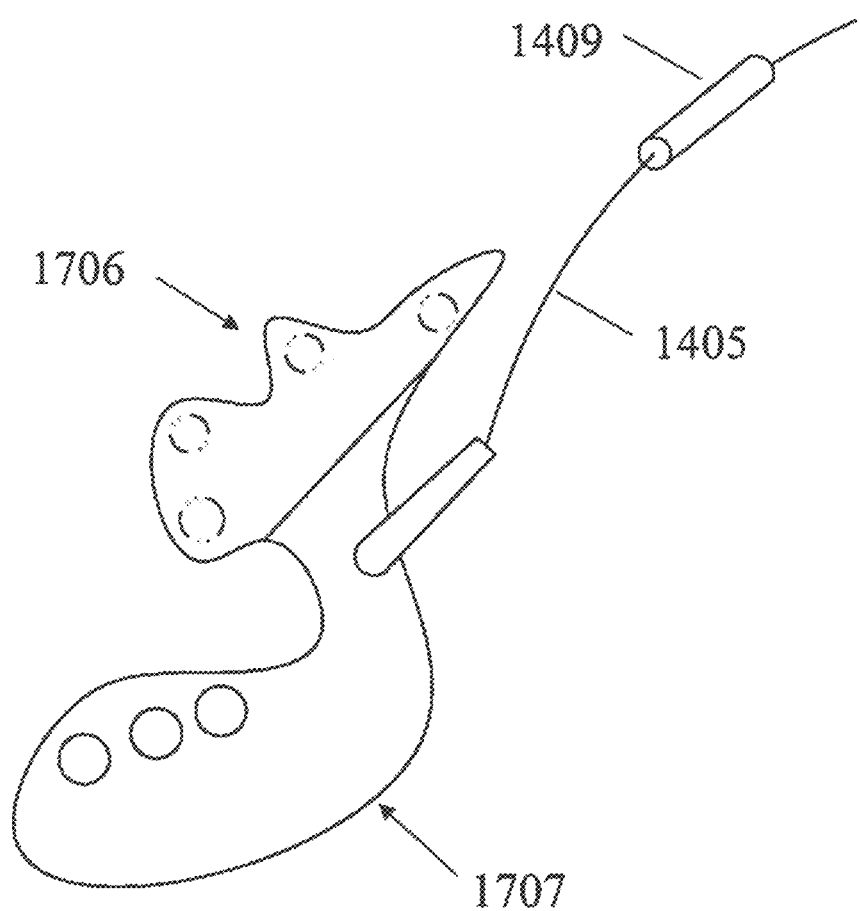

FIGS. 17 and 18 show further details of the embodiment of FIG. 14. According to this embodiment the sensor 1403 has a support 1701 comprising a magnetic shielding layer 1702 separating the sensor 1403 from the layer 1703 of magnetized material or a layer bearing or integrating one or more magnetic elements. The polarity of the said layer 1703 is inverted in relation to the polarity of a layer 1704 of magnetized material or bearing or integrating one or more magnetic elements which covers an intermediate layer 1705 forming a magnetic shield towards the inside of the probe. A pad 1706 of the keyboard 1707 is provided as an intermediate layer between the opposite polarized magnetized layers 1703 and 1704 respectively associated to the probe and to the sensor 1403. The pad 1706 may be provided with magnetized layers on the two opposite sides facing respectively the layer 1703 of magnetized material associated to the sensor 1403 and the layer of magnetized material associated to the probe which layers 1708 and 1709 are inversely polarized relatively to the said magnetized layers 1703 and 1704. The said pad has a form and dimensions substantially corresponding to the ones of the layers forming the magnetized layers 1703 and 1704. Thus when interposing the pad 1706 between the support of the sensor 1403 and the part of the joint associated to the probe, the probe, the pad 1706 and the support of the sensor attract each other and are releasably secured one to the other.

The present configuration may be provided also with mechanical reference pins as described in relation to the embodiment of FIG. 1 or with mechanical low profile coupling as describe with reference to the embodiment of FIG. 6.

According to a further feature of the embodiment of FIGS. 14, 17 and 18, the keyboard 1707 is linked to the pad 1706 by a lateral extension of the said pad which is bent relatively to the pad 1706 towards the probe body positioning the keyboard 1707 superposing on the lateral side of the probe body, i.e. the side whose tangent or secant is parallel to the minor axis of the cross-sectional shape of the probe along a plane perpendicular to the central axis of the probe, i.e. the axis passing through the transmit and receive window of the probe.

According to an example embodiment the said lateral extension is in the form of a curved arm following essentially the shape of the cross-section of the probe, thereby generating a further mechanical low profile coupling between keyboard and probe which combined with the magnetic force coupling.

One or more of the above describe embodiments is destined to be used in combination with different imaging technologies. One non limiting example for which the above combination of a probe and at least a sensor of a tracking unit is particularly relevant is the so called Virtual Navigator Real-time Fusion Imaging technology for enhancing real-time Ultrasound scans with second imaging modality 3D acquisitions, thereby supplementing MRI, CT, PET, PET/MRI, PET/CT, AngioCT, MRI TOF, 3D Ultrasound, 3D CEUS (Contrast Enhanced Ultrasound), 3D Color or Power Doppler data with morphological (B-Mode), hemodynamic (Color, Power, Continuous or Pulsed Wave Doppler), CEUS and stiffness (Elastosonography) data. Fusing together these real-time diagnostics supplied by Ultrasound with the highly detailed anatomical volumes (offered by MRI or CT), or functional (offered by PET. PET/MRI, PET/CT, AngioCT, MRI TOF, 3D Color or Power Doppler, 3D CEUS), allows the operator to display in real-time a virtual space where the different imaging modes are merged and where Ultrasound scanning plane spatial data is correlated with three-dimensional second imaging modality volumes. This allows for an easier navigation that is based on the geometrical and spatial relationships between the real-time data and pre-acquired data. The tool can be used for prevention, diagnosis, therapy, intervention and follow up. Virtual Navigator is based on electromagnetic tracking technology used in conjunction with Ultrasound probes (and biopsy instruments for instance) and accurate Motion Compensation Sensor. The Motion Control Sensor is placed on the body being examined to counteract voluntary and/or involuntary movements and to enable continuous motion compensation which preserves the previously set co-registration between two, or more than two, imaging modes.

Figure 8:
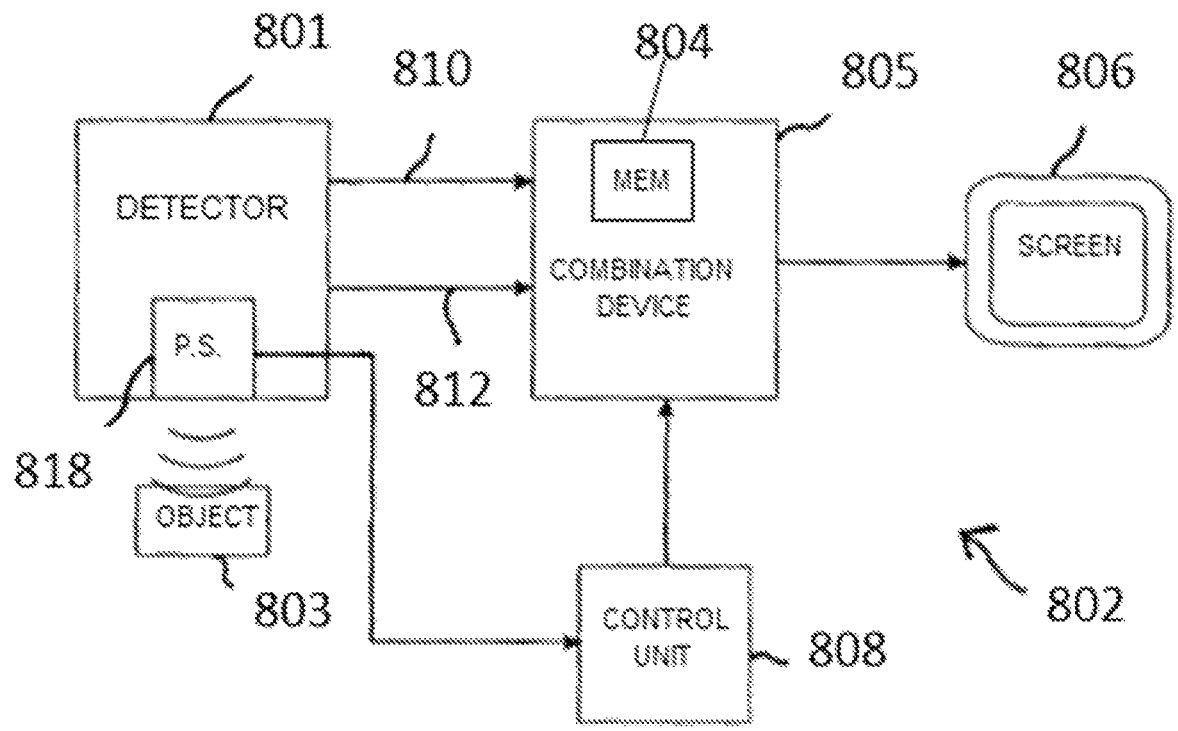
FIGS. 8 and 9 show block diagrams of an ultrasound system combined with a tracking system of the probe for generating images by combining ultrasound images and images acquired by a different imaging technique.
Figure 9:
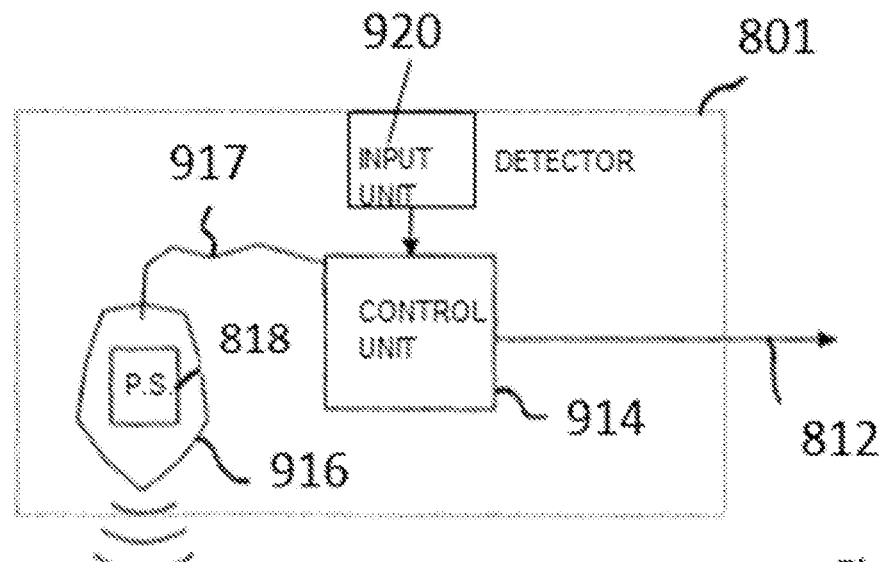

In FIGS. 8 and 9 an embodiment of a system for combining first and second image data of an object comprising an ultrasound imaging system and a tracking system of the ultrasound probe is shown. The ultrasound probe being provided with a sensor on its body for determining position, orientation and for tracking the displacements of the probe by processing the sensed signals by a processing unit of the tracking system.

According to this embodiment images of an object 803 (shown in FIG. 8) are to be displayed on a screen 806. An ultrasound detector 801 generates first image data of the object 803 and transfers the first image data to a combination device 805 via an image data connection 810. The combination device 805 comprises a data storage 804, which contains second image data that have previously been generated by a separate device (not shown in FIG. 8). The combination device 805 is adapted to combine the first and second image data and to display them on a screen 806, which is connected to the combination device 805. For example, the first and second image data may be displayed separately on a split screen or may be superimposed. In any case, it is preferred that a first image, which is generated using the first image data, and a second image, which is generated using the second image data, precisely show at least partially the same area or region of the object 803 in the same orientation (angle of view) and scaling (dimensions).

The ultrasound detector 1 and the combination device 805 are connected to each other by an additional data connection 812 for transferring geometry data from the ultrasound detector 801 to the combination device 805. In particular, the geometry data connection 812 may be connected (as shown in FIG. 9) to a control unit 914 of the ultrasound detector 801.

In practice, the data connections 810, 812 may be realised by separate data connection links or by the same data connection link. For example, a "link" may comprise a connection line, a plurality of connection lines and/or a digital data bus or bus system.

An ultrasound probe 916 (FIG. 9) of the ultrasound detector 801 is firmly coupled to a position sensor 818 of a tracking system. The determination of the orientation and the location of such a position sensor and, thereby, of the ultrasound probe is known in the art (see scientific publication of Pagoulatos et al.: "Interactive 3-D Registration of Ultrasound and Magnetic Resonance Images Based on a Magnetic Position Sensor", published in IEEE TRANSACTIONS ON INFORMATION TECHNOLOGY IN BIOMEDICINE, VOL. 3, NO. 4, December 1999). For example, magnetic and/or optical (e.g. infrared) signals may be used by the tracking system. The position sensor 818 is connected to a tracking system control unit 808 and the control unit 808 is connected to the combination device 805. During operation of the arrangement 802, the control unit 808 repeatedly or quasi-continuously transfers information concerning the position and concerning the orientation of the ultrasound probe 916 to the combination unit 805. Alternatively, this information may be transferred from the US detector to the combination device. I.e. this information might be at least partially included in the geometry data, which are transferred.

As shown in FIG. 9, the ultrasound device 801 may, for example, comprise an ultrasound probe 916, which is connected to the ultrasound control unit 914 via a flexible cord 917 for transferring echo signals to the control unit 914. On the other hand, the control unit 914 transfers control signals to the ultrasound probe via the cord 917. Also, it is possible that at least a part of the geometry information is transferred from the ultrasound probe 916 to the control unit 914 and/or that at least a part of the geometry information generated by the control unit 914 is based on and/or derived from information, which is transferred from the ultrasound probe 916 to the control unit 914. For example, the ultrasound probe 916 may be replaced and, therefore, transfers information concerning its identity to the combination device 805. In the combination device 805, in an additional unit of the arrangement 802, and/or in the combination device 805, information concerning the relative position and/or orientation of the specific ultrasound probe 916 relative to the position sensor 818 may be saved. For example, the ultrasound probe 16 may comprise a clip for attaching the position sensor 818. Therefore, it is possible to precisely position and orientate the position sensor 818 relative to the ultrasound probe 916 and to determine as well as to save the respective geometry data in advance. After replacement of the ultrasound probe 916, the identity information and the saved geometry information can be combined. As a consequence, it is not necessary to re-calibrate the arrangement consisting of the ultrasound detector 1 and the position sensor 818.

An input unit 920 is connected to the ultrasound control unit 914, for example for inputting settings of the ultrasound detector, such as a penetration depth or range of the ultrasound image. Further, the user may change the orientation of the ultrasound image via the input unit 920.

Figure 10:
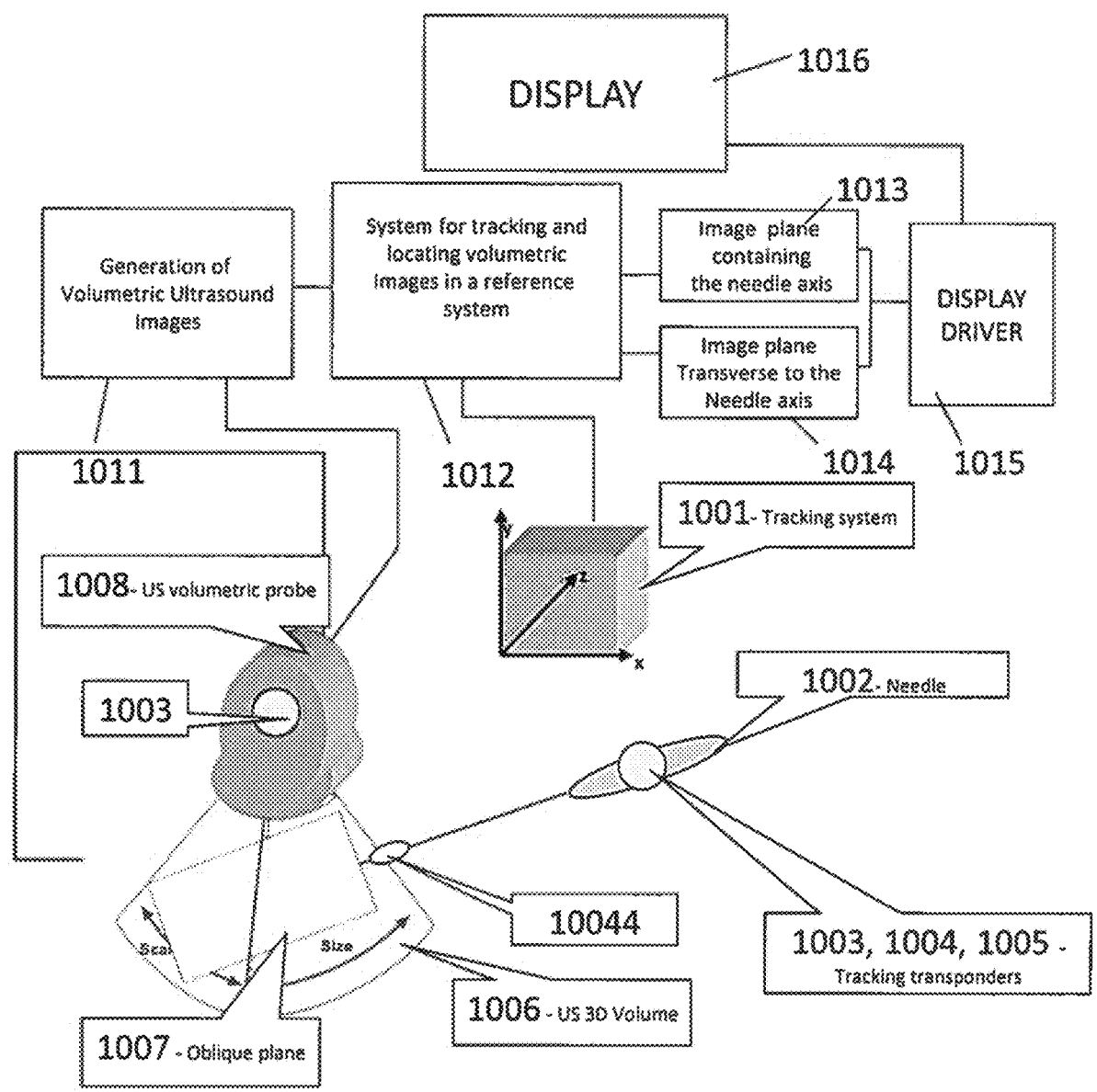
FIG. 10 shows a block diagram of a further embodiment of a biopsy needle or surgical tool imaging and tracking system comprising an ultrasound system in combination with a probe and/or biopsy needle or surgical tool tracking system.

A further embodiment requiring that at least one sensor of a tracking system has to be secured to an ultrasound probe is the system for guiding surgical tools by real-time ultrasonic imaging which is very schematically shown in FIG. 10.

Numeral 1008 designates an ultrasonic scan probe which is connected to a probe control unit for ultrasonic imaging and particularly for generating volumetric ultrasound images.

A variety of volumetric ultrasound imaging methods are known. According to an embodiment of this method, the probe is provided in combination with a tracking system which detects the position, orientation and displacement of the probe. A succession of ultrasound images is acquired as the probe is moved, said images being grouped into a 3D image composed of the various 2D images acquired at different probe positions along the displacement path, which positions are detected by the tracking system. Thus, the 2D images can be arranged in relative order to form a 3D image.

Tracking systems are known and widely used for the purpose of acquiring a 3D ultrasound image. An example of tracking system is the system sold by Ascension Technology with the trade name PCI Bird which is incorporated in a currently available product, sold by the owner hereof with the name of "Virtual Navigator".

In the scheme of FIG. 10, the tracking system is represented by the coordinate system designated by numeral 1001. The tracking system actually defines the various positions of the probe 1008 with reference to a predetermined initial reference point and is thus the operating unit that defines a reference system describing the probe displacement space.

In principle, there is no limitation as for the type of probe to be used, provided that it can cover a slice area large enough to contain the image to be acquired. Nonetheless, as shown in FIG. 1, advantages are achieved from using a volumetric probe. A volumetric probe may be as disclosed in EP 1 681 019 and in EP 1 167 996 by the owner hereof.

Thus, when the size of the subject to be imaged by ultrasound allows to do so, the probe is not required to be manually displaced by the operating personnel or a specially dedicated device. In other cases, the volumetric probe can be displaced less often and to few different positions, in which it can be held during automatic acquisition of the volumetric image that the probe can generate without being displaced.

In this case, the tracking system 1001 is only used to define the different probe position/s in the space described by the reference system generated or defined by the tracking system 1001 itself.

The tracking systems require at least one detector to be mounted to the element whose displacement or position is to be monitored, which marker/detector, with reference to the tracking system used herein, is a transponder. A transmitter-receiver unit can detect the marking transponder and determine the probe position. The marker means associated with the probe 1008 are designated by numeral 1003. Numeral 1006 designates the volumetric image acquired by the volumetric probe 1008. Numeral 1002 designates a surgical tool and particularly a needle or similar elongate, rod-like element. These tools may include, for example, biopsy needles, cannulas for insertion of a variety of devices, thermos-ablation needles or the like.

The needle or rod-like element has a characteristic functional axis, and in this case this axis is the axis of the needle which coincides with the insertion axis. Different types of tools may have different characteristic functional axes. For example, in the case of a surgical knife, the characteristic working axis may be the cutting edge of its blade. The characteristic functional axis of a particular type of tool can be determined in an intuitive and simple manner.

The needle 1002 may carry a single sensor or marking transponder, which is sufficient to determine the position of the tool and its orientation, particularly with reference to the characteristic working or functional axis of said needle which, as mentioned above, is the central longitudinal axis of the needle. The sensor or markers may be attached to the biopsy needle, particularly to the handle thereof in a similar way as the sensor or markers on the probe body.

However, according to an improvement shown in the Figures described herein, the tool, i.e. the needle 1002 carries two or more sensors or marking transponders, designated by numerals 1003, 1004. This improvement allows detection of any needle bending, which can be thus accounted for while operating the system.

Therefore, in the case of the needle 1002 of the Figures, two transponders are located at a certain distance from each other, coincident with the needle axis, and can be used to determine the needle orientation with particular reference to the insertion direction, as well as any deformation, particularly bending or curving of the needle. When a transponder is mounted directly to the tip or at a predetermined distance therefrom, the position of the needle tip can be determined upon insertion into the body under examination.

The sensor or transponder at the tip of the needle 1002, here the transponder 1004, shall not necessarily be placed at the tip but, as mentioned above, it may be located at a predetermined known distance from the tip. In this case, once the position of the transponder 1004 has been detected, the position of the tip may be determined by a simple arithmetic operation.

Numeral 1007 designates a cutting plane of the 3D image that has a predetermined inclination relative to the characteristic functional axis, i.e. the longitudinal central axis, i.e. the direction of insertion of the needle 1002.

A 2D image of the object is generated along said cutting plane, using the image data of the 3D image. This process consists in determining the subset of voxels of the 3D image that falls within the predetermined cutting plane 1007, to generate a 2D image. This may occur in a known manner, as disclosed for instance in the above mentioned patent applications by the applicant hereof, and particularly in EP 1 167 996.

Processing occurs in a control and processing unit typically incorporated in ultrasonic imaging apparatus, which substantially consists of a processing unit that stores and executes special ultrasound apparatus control programs for transmitting and receiving ultrasound signals, for focusing the ultrasound signals transmitted by the probe and the ultrasound signals received by the probe upon reflection of the transmitted signals, for converting the received signals into image data and for generating and displaying images on a monitor, as well as for monitoring the execution of other operations that depend on the ultrasound signal acquisition and processing mode being used. The processing unit also controls the tracking system, which may be provided as software or dedicated hardware controlled by said software.

In FIG. 10, the processing unit is designated by its functional blocks only, which are generally used to execute the operations of example embodiments of the present disclosure. Thus, the block 1011 generally includes all hardware and software units required for 3D imaging (see also EP 1 681 019 and EP 1 167 996). Thanks to the tracking system, the 3D image is assigned a well-defined position in a reference Cartesian system, which is defined by the tracking system that detects the position of the probe 1008. The tracking system simultaneously detects the position of the needle or other tool 1002 and the orientation of the characteristic functional axis of such tool 1002 with reference to the same reference system defined by the tracking system. This will provide well-defined relative positions between the volumetric image and the position and orientation of the tool 1002, i.e. the characteristic functional axis thereof. In these conditions, a cutting plane may be defined in the 3D or volumetric image generated by the probe 1008, which plane has a predetermined inclination relative to the characteristic functional axis of the tool 1002.

Multiple cutting planes may be also defined, having predetermined and different positions and orientations relative to said characteristic functional axis of the tool 1002.

Particularly, referring to the needle, a cutting plane may be defined, which is oriented perpendicular to the characteristic functional axis of the tool 1002 and is at a predetermined distance from the internal or front end tip, with reference to the direction of insertion of the needle. In this case, the image generated along said cutting plane and reconstructed from the volumetric image data, i.e. the voxels that fall within such cutting plane will be as viewed by an observer situated at the tip of the needle and looking towards the longitudinal axis of the needle in the direction of insertion of the latter. Alternatively to or in combination with the above, images may be also generated along different cutting planes. A possible additional cutting plane might be the plane that contains the longitudinal axis of the needle 1002, with the path of the needle into the body under examination being thus visible.

The images obtained along the various cutting planes may be displayed in succession, i.e. alternate to each other or in side-by-side or simultaneous arrangement. This condition is shown by the functional blocks 1013 and 1014, which designate all hardware and software units required to define the above mentioned cutting planes and generate images along said cutting plane, as well as simultaneously or alternately display them using display drivers 1014 on the display 1015.

Figure 19:
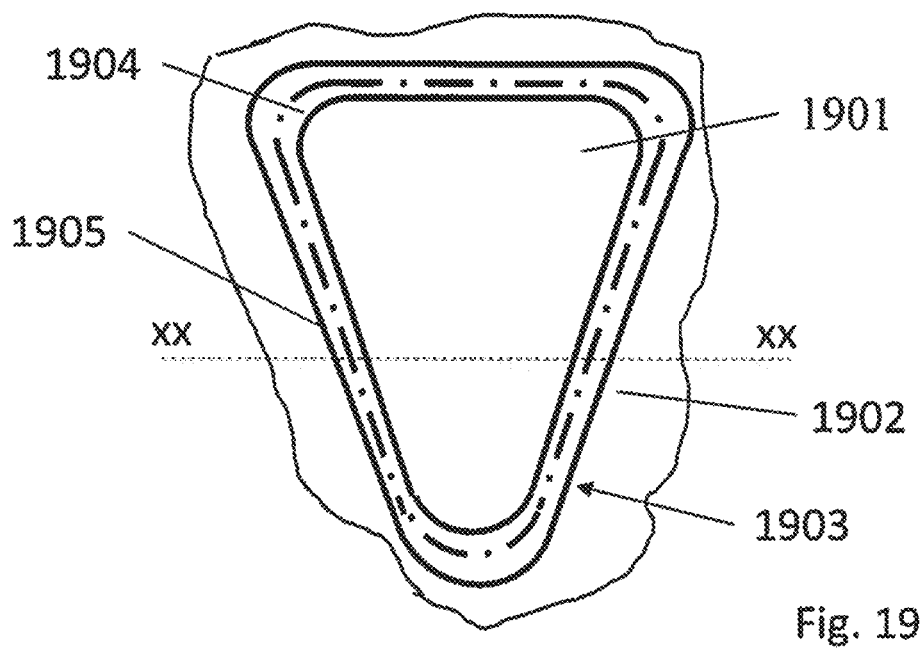
Figure 20:
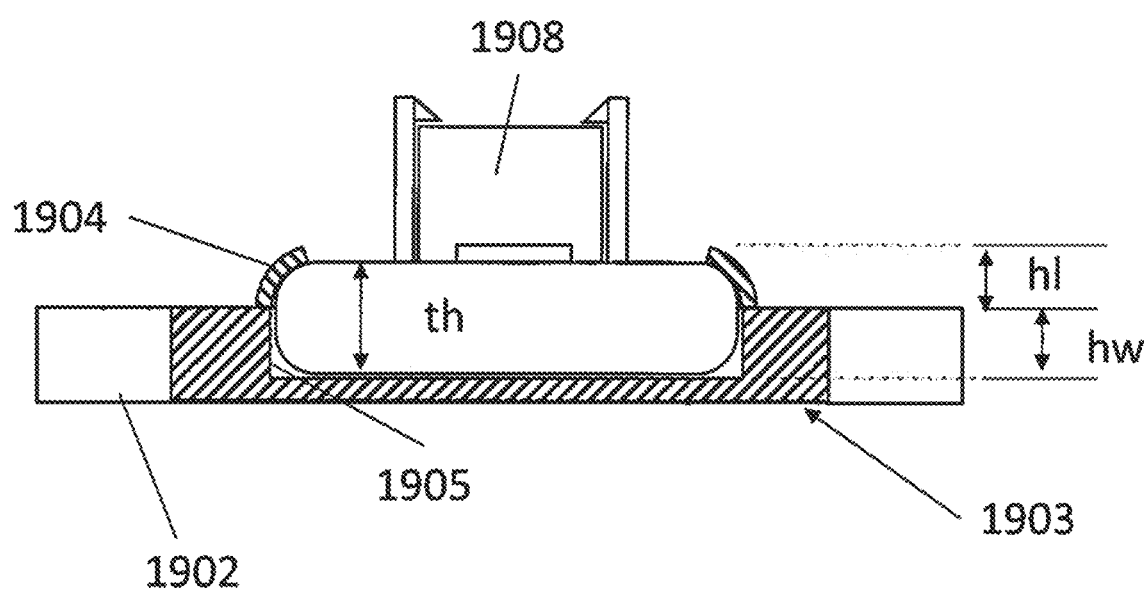

Referring to FIGS. 19 and 20, a first embodiment of a mechanical coupling part of the support 1901 of a sensor to the wall 1902 of the case of a probe is shown. FIG. 19 is a top view on a support 1901 engaged in a seat 1903 on the wall 1902 of the probe. The contour of the support 1901 is shown with a discontinuous line since it is overlapped by a lip of elastic deformable material 1904 provided at least at the top end of the lateral wall 1905 of the seat 1903.

FIG. 20 is a cross section along a plane coinciding with the line XX-XX in FIG. 19. According to the drawings, the seat 1903 is formed by an indentation provided in the wall 1902 of the probe and being opened at the side facing away from the inner of the probe case. The indentation having a bottom wall which construction is configured according one of the previously described embodiments for the magnetic coupling, such as the layered configuration providing a magnetic shield layer and a layer bearing magnetic elements which are polarized in such a way as to exercise an attraction force of the support bearing oppositely polarized magnetic elements shielded towards the sensor secured to the said support.

The height hw of the lateral walls 1905 of the indentation covers at least part of the thickness th of the support 1901. From the upper end of the lateral wall a lip 1904 of elastic deformable material protrudes in the direction opposite to the bottom wall of the seat 1903 having an height h1 such that it covers the resting part of the thickness th of the support 1901 left free by the lateral wall 1905 of the indentation while protruding at the same time in the direction of the inner of the indentation 1903 reducing the dimensions of the opening of the said indentation to a dimension smaller than the peripheral contour of the support 1901 and partially overlapping a peripheral zone of the surface of the support 1901 opposite to the bottom of the indentation and along the lateral walls of the support 1901 facing the lateral walls 1905 of the said indentation. The said lip 1904 being dimensioned and shaped relatively to the shape of the support ant to the dimensions of the support in such a way to allow a releasable coupling of the support in the seat 1903 of the snap-fit kind.

Although the example of FIG. 20 shows a support according to the embodiment of FIG. 6 in which the sensor 1908 is mechanically, releasably coupled to the support 1901 by snap fit coupling means, the above embodiment of the mechanical coupling of the support 1901 to the wall of the probe can be provided, mutatis mutandis, in combination with any of the previously disclosed embodiments.

Different variant embodiments are possible. In one variant embodiment, the height hw of the lateral walls 1905 may correspond to the thickness th of the support, the lip 1904 protruding essentially from the upper edge of the lateral wall

1905 of the indentation in such a way as to overlap a peripheral zone of the side of the support 1901 opposed to the side facing the bottom of the seat.

In a further variant embodiment, the seat does not include an indentation but a lateral wall 1905 protrudes from the outer surface of the wall 1902 of the probe. In this case two alternatives may be possible. In a first alternative the lateral wall delimiting the seat is entirely made of elastic deformable material having a height corresponding to the sum of the height hw and hl of the embodiment of FIG. 20 and forming the lateral wall 1905 and the lip 1904 by one piece. The said lateral wall may be molded or co molded on the surface of the wall 1902 of the probe. A variant provides a lateral wall 1905 molded on top of the wall of the probe and made of a rigid material as the same one of the wall of the probe with a height hw according to the embodiment of FIG. 20 which lateral wall 1905 is prolonged at its edge opposed to the probe wall 1902 by the lip 1904 having a height and a shape according to the example of FIG. 20.

FIG. 21 shows a variant embodiment of the embodiment of FIG. 19 in which instead of a continuous lip 1904 a crown of teeth 2100 is provided. Each tooth having a configuration according to the cross section of the lip 1904 of FIG. 20.

In the embodiment of FIG. 22, instead of a continuous lip 1904 as in FIG. 19, a combination of segments 2200 of a lip distributed along the upper edge of the lateral wall of the seat are provided. The non-limiting example of FIG. 22 provides lip segments 2200 at each corner of the area delimited by the lateral walls of the seat and of the support.

Also, the teeth or the segments of the lip of the examples of FIGS. 21 and 22 may be configured according to the different variant embodiments described above in relation to the embodiment of FIG. 20.

FIG. 23 show a variant embodiment of the snap parts for attaching in a releasable way the support to the probe. According to this embodiment, the lateral walls 2305 of the seat 2303 and the lateral walls 2309 of the support 2301 are provided with cooperating coupling parts of the snap fit kind. The lateral walls 2305 of the seat 2303 are provided with protrusion 2015 protruding towards the inside of the seat 2303 and thus the facing lateral walls 2309 of the support 2301 which protrusion 2015 has a rounded cross section. The lateral walls 2309 of the support 2301 show a groove 2319 having a cross section corresponding to the cross section of the protrusion 2315 and positioned such that the protrusion 2315 snaps inside the groove 2319 when the support is pressed towards the probe in a aligned position with the seat.

The dimensions of the grove and the protrusion may be such that the intrinsic elastic behavior of the material of the support 2301 and of the lateral walls 2305 of the seat 2303 are sufficient to allow the releasable snap-fit. Alternatively, the protrusion 2315 may be made of a different material than the one of the wall of the probe such as an elastic deformable or compressible material and is over-molded on the surface of the said lateral wall 2305 of the seat 2303.

Similarly to the example of FIGS. 19 to 22, the protrusion 2315 and/or the groove 2319 can by a continuous one or be formed by a combination of segments of protrusion and/or of corresponding grooves or by a crown of knobs and/or corresponding notches.

Similarly to the previous embodiment of FIG. 20, the said seat may be formed partly by an indentation in the wall of the probe and partly by a wall prolonging the lateral walls of the indentation in order to cover the entire thickness of the support or at least to provide the said protrusions 2315 at a height coinciding with the groove 2319 on the lateral wall 2309 of the support 2301.

According to the example of FIG. 23, the seat is molded on top of the externa surface of the wall 2302 of the probe. In this embodiment, the seat has lateral walls 2305 and a bottom wall integer with the said lateral walls which are attached to the outer surface of the wall 2302 of the probe. It has to be noted that this construction of the seat can be provided in combination also with the pervious examples of FIGS. 19 to 22.

Also in the case of the embodiment of FIG. 23 the support 2301 is configured according to the embodiment of FIG. 6 in which the sensor 2308 is mechanically, releasably coupled to the support 2301 by snap fit coupling parts, the above embodiment of the mechanical coupling of the support 2301 to the wall of the probe can be provided, mutatis mutandis, in combination with any of the previously disclosed embodiments.

The above embodiments of the mechanical coupling of the support to the probe have been described in relation to the support for a sensor. According to the previous embodiments the construction of this mechanical coupling part can be provided also on the supports or pads of other operative units such as for example also the keyboard described with reference to FIGS. 17 and 18.

Figure 24:
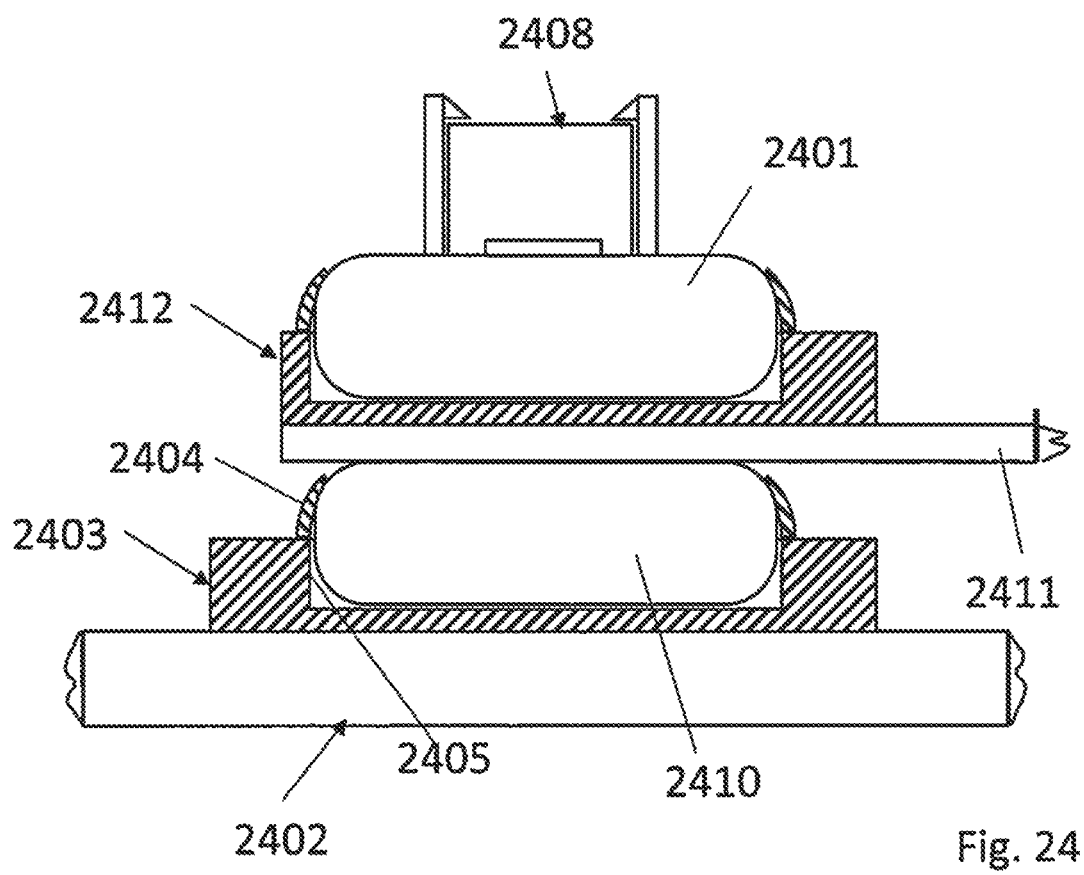
Figure 25:
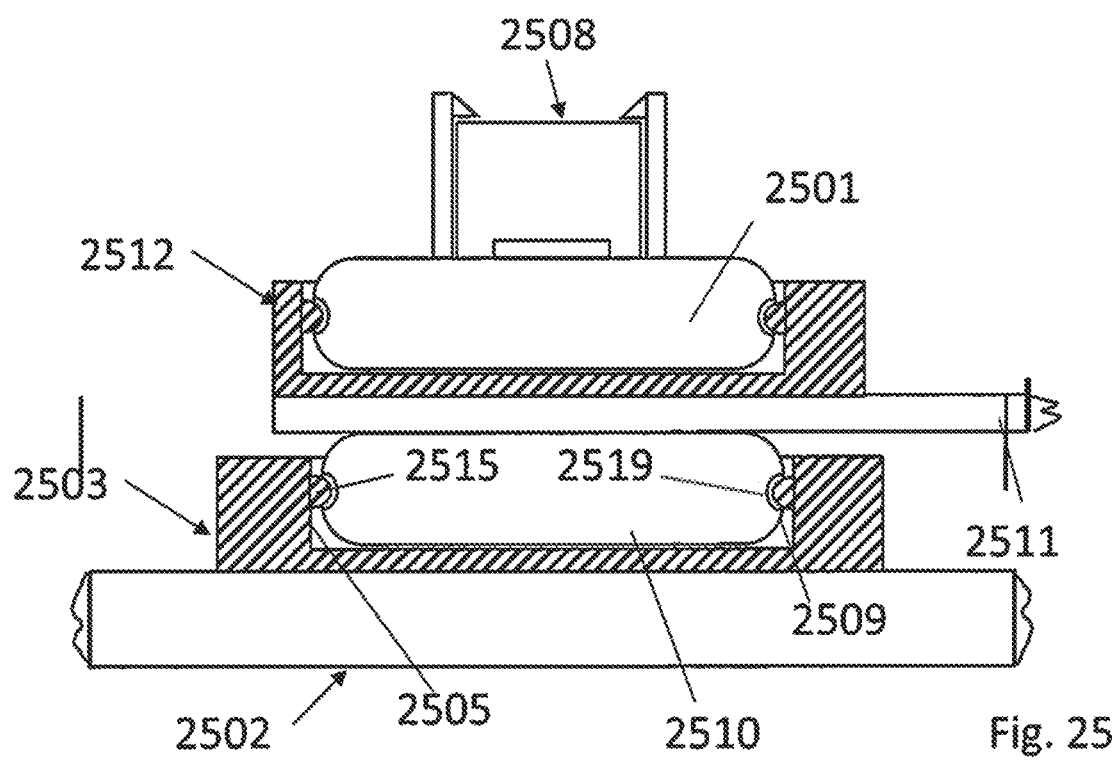

FIGS. 24 and 25 show the cross section according to a plane perpendicular to the wall of the probe of the mechanical coupling part according to the embodiments of FIGS. 19 to 23 applied to the embodiment of FIGS. 17 and 18, in which a sensor and a keyboard are releasably attached to the probe, the keyboard being provided with a coupling pad and the sensor with a support and the said coupling pad and the said support being releasably attached respectively to the probe and one to the other in an overlaid configuration.

The embodiments according to FIGS. 24 and 25 are shown in combination with the variant configuration of the seat in which the said seat is provided with a lateral wall and a bottom wall which are molded over the outer surface of the wall of the probe and of the coupling pad of the keyboard. Nevertheless, each of the above disclosed variants in relation to FIGS. 19 to 23 can be provided, mutatis mutandis, in any combination with the embodiment of FIGS. 24 and 25.

FIG. 24 shows a wall 2402 of the probe to which a seat 2403 is secured by co-molding or chemical/physical bonding. The seat 2403 cooperates with the coupling pad 2410 of a keyboard which is supported on a lateral side of the probe by an arm 2411 according to the configuration of FIGS. 17 and 18. The arm 2411 departs from the coupling pad 2410. The seat 2403 is configured according to the embodiment of FIGS. 19 to 22, the lateral wall 2405 of the seat being prolonged by a lip a combination of segments of lips or a crown of teeth 2404 of elastic deformable material.

The seat 2403 may be also configured according to any of the variants related to the embodiment of FIGS. 19 to 22.

The coupling pad 2410 is provided on its side opposing the probe with a seat 2412 of the snap fit kind destined to cooperate with the support 2401 or with a coupling pad of a sensor 2408 or of another operating unit. The seat 2412 of the snap fit kind on the coupling pad 2410 may be identical to the one 2403 of the probe or it can have a different configuration, as for example a configuration according to the embodiment of FIG. 23 or of any variant embodiments of it, provided the support 2401 of the sensor 2408 is configured in a matching way.

In the embodiment shown the seat 2403 on the probe and the one 2412 on the coupling pad 2410 are identical and the coupling pad 2410 and the support 2401 are also identical. This has the advantage that the sensor can be attached to the probe without the presence of the coupling pad of the further operating unit, i.e. the keyboard, or the sensor can be attached to the coupling pad of the keyboard while this is attached to the probe. Furthermore, providing a different construction of the support 2401 for the sensor, for example by providing a supporting arm to which the sensor 2408 is secured and which places the sensor in a position not interfering with a further coupling pad or a further support also the support 2401 could be provided with a seat similarly to the coupling pad 2410.

Furthermore, one or more different coupling pads of one or more further operating units may be attached one to the other when each coupling pad of the said operating units is configured according to the one disclosed in FIG. 24.

FIG. 25 shows the embodiment of FIG. 24 in which the mechanical coupling parts of the snap-fit kind are configured according to the example of FIG. 23, both for the coupling pad 2510 for the keyboard or an operating unit and for the support 2501 for the sensor 2508.

A seat 2503 is provided on the probe wall 2502, while an identical seat 2512 is provided on the side of the coupling pad 2510 opposed to the probe. Also here the two seats 2503 and 2512 are identically configured while also the support 2501 for the sensor 2508 and the coupling pad 2510 for the keyboard or for another operating unit are identical in shape and dimensions in order to be able both to be engaged directly and alternatively to the seat 2503 on the probe or to one another as illustrated in FIG. 25.

The lateral walls 2505 of the seats 2503 and 2512 are provided with the protrusion 2515 cooperating with a groove 2519 on the lateral wall 2509 of the support 2501 and of the coupling pad 2510.

Also in this case the protrusions 2515 and the grooves 2519 can be continuous, or a combination of segments of protrusions and corresponding segments of groves or a crown of knobs and corresponding notches.

The embodiment according to FIG. 25 can be provided, mutatis mutandis, in combination with each embodiment disclosed in relation to the embodiment illustrated in FIG. 23.

The invention claimed is:

1. A joint having two parts provided respectively on an ultrasound probe and at least one operating unit, the ultrasound probe used in combination with the operating unit, the probe comprising a wall defining at least part of a case of the probe and the case having an interior, the operating unit chosen from a tracking sensor or receiver and/or a keypad and/or a surgical tool support, the two parts of the joint being releasably engageable with each other by magnetic force and by mechanical coupling;

wherein the part of the joint provided on the probe comprises magnetic elements that are distributed along an area of the wall according to a pattern and each has a predetermined polarity, and a first magnetic shield comprising a surface covering the magnetic elements and an opposite surface oriented towards the interior of the case;

wherein the part of the joint provided on the operating unit comprises a pad having magnetic elements that are distributed according to a predetermined pattern thereon and each has a predetermined polarity that is complementary to a corresponding one of the magnetic elements on the wall of the probe, the magnetic elements on the pad being provided on the side of the pad facing the probe, and a second magnetic shield comprising a surface that faces toward the operating unit and covers the magnetic elements on the pad and an opposite surface that faces away from the operating unit; and wherein the magnetic force is due to the magnetic elements provided on the probe, and the magnetic elements provided on the pad that is part of the joint associated with the operating unit, operating as magnetic field sources, and the first magnetic shield on the probe and the second magnetic shield provided to the operating unit are configured, respectively, to shield their corresponding magnetic field sources respectively towards the probe and towards the operating unit.

2. The joint according to claim 1, wherein the part of the joint provided on the probe is alternatively secured to the case of the probe in a non-releasable or releasable way or integrated into a portion of the probe.

3. The joint according to claim 1, wherein the part of the joint associated with the operating unit is integrated or non-releasably secured to the operating unit, particularly to a case of the operating unit or a part of the case of the operating unit.

4. The joint according to claim 1, wherein a total force securing the operating unit to the probe is in part magnetic and in part mechanical, the total force retaining one of the two parts of the joint as engaged with the other one of the two parts of the joint.

5. The joint according to claim 1, wherein a guide for correct positioning of the two parts of the joint is provided, the guide being formed by the magnetic force between the two parts of the joint.

6. The joint according to claim 1, wherein centering components between the two parts of the joint are provided, the centering components forming or are a part of the mechanical coupling between the two parts of the joint.

7. The joint according to claim 1, wherein in combination with the first magnetic shield on the probe and the second magnetic shield provided to the part of the joint associated with the operating unit, corresponding ones of the magnetic elements distributed according to a predetermined pattern on each of one the part of the joint on the probe and the part of the joint associated with the operating unit have opposed polarity so that the part of the joint on the probe and the part of the joint associated with the operating unit are attracted to hold one part of the joint against the other part of the joint.

8. The joint according to claim 1, wherein the first magnetic shield of the part of the joint provided on the probe comprises a layer of magnetic insulating material having a predetermined dimension and shape, wherein said layer is laid over the surface of the wall facing the interior of the probe, the magnetic elements being distributed according to a predefined pattern between the layer of magnetic insulating material and the wall of the case of the probe.

9. The joint according to claim 1, wherein the portion of the probe comprises a handle portion of the probe.

10. An ultrasound system comprising a probe and a probe tracking system having at least one tracking sensor secured to the probe, the probe comprising a wall defining at least part of a case of the probe and the case having an interior, wherein the tracking sensor is secured to the probe in a releasable way by a joint comprising at least two parts, one part of the joint being associated with the probe and the other part of the joint being associated with the tracking sensor, the two parts of the joint being releasably engageable one with the other by magnetic force and by mechanical coupling;
  wherein the part of the joint provided on the probe comprises
    at least one probe magnetic element having a predetermined polarity, and
    a first magnetic shield comprising a surface covering the at least one probe magnetic element and an opposite surface oriented towards the interior of the case;
  wherein the part of the joint provided on the tracking sensor comprises
    at least one tracking sensor magnetic element having a predetermined polarity that is complementary to a corresponding one of the at least one probe magnetic element of the probe, and
    a second magnetic shield comprising a surface that faces toward the tracking sensor and covers the at least one tracking sensor magnetic element; and
  wherein the magnetic force is due to the at least one probe magnetic element, and the at least one tracking sensor magnetic element, operating as magnetic field sources, and the first magnetic shield and the second magnetic shield are configured, respectively, to shield their corresponding magnetic field sources respectively towards the probe and towards the tracking sensor.

* * * * *